United States Patent
Abed et al.

(10) Patent No.: US 12,280,083 B2
(45) Date of Patent: Apr. 22, 2025

(54) **EXTRACTS OF *MORICANDIA* FOR THE USE THEREOF IN THE PREVENTION AND TREATMENT OF METABOLIC DISEASES**

(71) Applicants: UNIVERSITÉ DE BOURGOGNE, Dijon (FR); CENTRE NATIONAL DE LA RECHERCHE SCIENTIFIQUE, Paris (FR); INSTITUT NATIONAL DE LA RECHERCHE POUR L'AGRICULTURE, L'ALIMENTATION ET L'ENVIRONNEMENT, Paris (FR); UNIVERSITÉ DE MONASTIR, Monastir (TN)

(72) Inventors: Basma Abed, Ghomrassen Tataouine (TN); Corinne Leloup, Messigny et Vantoux (FR)

(73) Assignees: UNIVERSITÉ DE BOURGOGNE, Dijon (FR); CENTRE NATIONAL DE LA RECHERCHE SCIENTIFIQUE, Paris (FR); INSTITUT NATIONAL DE LA RECHERCHE POUR L'AGRICULTURE, L'ALIMENTATION ET L'ENVIRONNEMENT, Paris (FR); UNIVERSITÉ DE MONASTIR, Monastir (TN)

(*) Notice: Subject to any disclaimer, the term of this patent is extended or adjusted under 35 U.S.C. 154(b) by 976 days.

(21) Appl. No.: 17/272,739
(22) PCT Filed: Sep. 10, 2019
(86) PCT No.: PCT/FR2019/052092
§ 371 (c)(1),
(2) Date: Mar. 2, 2021
(87) PCT Pub. No.: WO2020/053519
PCT Pub. Date: Mar. 19, 2020

(65) Prior Publication Data
US 2021/0346449 A1 Nov. 11, 2021

(30) Foreign Application Priority Data
Sep. 10, 2018 (FR) .................. 1858094

(51) Int. Cl.
*A61K 36/31* (2006.01)
*A23L 33/105* (2016.01)
(Continued)

(52) U.S. Cl.
CPC .............. *A61K 36/31* (2013.01); *A23L 33/18* (2016.08); *A61K 36/481* (2013.01); *A61P 3/10* (2018.01)

(58) Field of Classification Search
None
See application file for complete search history.

(56) References Cited

U.S. PATENT DOCUMENTS 8,946,283 B2   2/2015   Park et al.

FOREIGN PATENT DOCUMENTS

CN   1726953 A   * 2/2006 ........... A61K 36/481

OTHER PUBLICATIONS

Labed et al. Compounds from the pods of Astragalus armatus with antioxidant, anticholinesterase, antibacterial and phagocytic activities. Pharmaceutical Biology, 2016, vol. 54, No. 12, 3026-3032 (Year: 2016).*

(Continued)

*Primary Examiner* — Lakshmi S Channavajjala
(74) *Attorney, Agent, or Firm* — Maier & Maier, PLLC

(57) ABSTRACT

A composition including an extract of *Moricandia* for the use thereof in the prevention and/or treatment of metabolic diseases related to impaired glucose tolerance and/or insulin resistance. Also a composition including an extract of *Moricandia* for the use thereof in the prevention of weight gain, in particular of body fat.

15 Claims, 10 Drawing Sheets

(51) Int. Cl.
    *A23L 33/18*     (2016.01)
    *A61K 36/481*     (2006.01)
    *A61P 3/04*     (2006.01)
    *A61P 3/10*     (2006.01)
    *A61P 5/50*     (2006.01)

(56) References Cited

OTHER PUBLICATIONS

Braham et al., "Antioxidant Phenolic Glycosides from Moricandia arvensis". J Nat Prod. Apr. 2005 68(4):517-22.

Bratkov et al., "Flavonoids from the Genus *Astragalus*: Phytochemistry and Biological Activity". Pharmacogn Rev. Jan.-Jun. 2016 10(19):11-32.

Marrelli et al., "Phytochemical and Biological Profile of *Moricandia arvensis* (L.) DC.: An Inhibitor of Pancreatic Lipase". Molecules. Oct. 31, 2018. 23(11):2829. 15 pages.

Skandrani et al., "Antigenotoxic and Free Radical Scavenging Activities of Extracts from Moricandia arvensis". Drug Chem Toxicol. 2007. 30(4):361-82.

Skandrani et al., "Moricandia arvensis extracts protect against DNA damage, mutagenesis in bacteria system and cavenge the superoxide anion". Toxicol In Vitro. Feb. 2009 23(1):166-75.

Skandrani et al., "Assessment of phenolic content, free-radical-scavenging capacity genotoxic and anti-genotoxic affect of aqueous extract prepared from Moricandia arvensis leaves" Food Chem Toxicol. Feb. 2010 48(2):710-5.

Skandrani et al., "Leaf and root extracts of Moricandia arvensis protect against DNA damage in human lymphoblast cell K562 and enhance antioxidant activity". Environ Toxicol Pharmacol. Jul. 2010 30(1):61-7.

Soliman et al., "Anti-Helicobacler Pylori, Anti-Diabetic and Cytotoxicity Activity of Biosynthesized Gold Nanoparticles Using Moricandia Nitens Water Extract". Egypt J Chem. 2018. 61(4):691-703.

\* cited by examiner

EXTRACTS OF *MORICANDIA* FOR THE USE THEREOF IN THE PREVENTION AND TREATMENT OF METABOLIC DISEASES

FIELD

The present invention relates to a composition comprising an extract of *Moricandia*, for use in the prevention and/or treatment of metabolic diseases related to glucose intolerance and/or insulin resistance. It also relates to a composition comprising an extract of *Moricandia*, for use in the prevention of weight gain, in particular fat mass.

BACKGROUND

Metabolic diseases and their consequences are among the most common causes of death in the world. Heart diseases, a comorbidity of diabetes, is a leading cause of death—they account for 32% of all deaths—ahead of cancer and chronic respiratory disease, this global scourge affects more than 100 million people and experts predict that it will cause more than 25 million deaths in 2030, against 17.5 million in 2005. Today, metabolic syndrome is so prevalent that an estimated one in four adults in the United States is affected by it; in Europe, it affects 15% of adults.

Type 2 diabetes, or non-insulin-dependent diabetes, is the most common form of diabetes, affecting about 90% of diabetic people. The disease affects all age groups but its frequency increases with age. For example, the frequency of the disease reaches 25% over the age of 65 in the United States; and over 75 in France. Globally, the incidence of diabetes in adults has increased from 4.7% in 1980 to 8.5% in 2015. Mortality directly associated with diabetes is estimated to 1.6 million deaths per year. In addition, recent studies have shown that diabetes is accompanied, in 60% of cases, by the appearance of many other metabolic risk factors such as hypertension, overweight or even obesity, and dyslipidemia. The search for a treatment for type 2 diabetes therefore remains a major challenge today.

Diabetes is a metabolic disease characterized by a chronic excess of sugar in the blood (hyperglycemia), corresponding to a fasting glycemia (level of glucose in the blood) higher than 1.26 g/L. In a non-pathological context, glycemia is kept constant by:

(i) the absorption of carbohydrates from food in the intestines;
(ii) the storage of glucose, via the secretion of insulin by the endocrine pancreas which stimulates the absorption of glucose by so-called "insulin-sensitive" tissues, mainly muscles, adipose tissue and the liver; and
(iii) the release of glucose into the blood, mainly by the liver, during the interprandial period.

Insulin resistance, i.e, when the response of cells to insulin is reduced, in particular following the appearance of a low-grade inflammatory state, most often linked to an over-developed visceral fat mass, is also accompanied by a defect of inhibition of hepatic glucose production. As glucose uptake is reduced, this condition leads to the onset of type 2 diabetes. The endocrine pancreas (composed of the islets of Langerhans) can compensate for this resistance initially by secreting more insulin, but following this excessive demand leading to the exhaustion of the pancreas, an insulin deficiency (i.e, a synthesis defect of insulin by the islets of Langerhans β cells) sets in. This deficiency then requires insulin therapy.

Other pathologies are associated with glycemic deregulation, such as metabolic syndrome, diseases related to insulin resistance or related to insulin deficiency, glucose intolerance, hyperglycemia, obesity, dyslipidemia, hypercholesterolemia, hypertriglyceridemia and oxidative stress.

The treatment of diseases associated with glycemic deregulation, beyond dietary recommendations and increased physical activity, is based on the injection of insulin or on the use of hypoglycemic agents such as sulfonylureas, which stimulate insulin secretion; biguanides (such as metformin, phenformin and buformin), which improve insulin sensitivity; α-glucosidase inhibitors, which slow down the digestion of sucrose and complex carbohydrates; and thiazolidinediones which, in combination with insulin therapy, decrease insulin resistance.

However, these therapeutic approaches are associated with many side effects. For example, the administration of sulfonylureas can lead to hypoglycemia, kidney and liver diseases, increase the risk of cardiovascular events, trigger unwanted skin reactions, dizziness and headaches. Lactic acidosis and increased risk of cardiovascular disease are also side effects of biguanides. α-glucosidase inhibitors can lead to hypoglycemia and gastrointestinal disturbances. Finally, among the drawbacks frequently associated with the use of thiazolidinediones are the dependency of their effectiveness on the presence of insulin, the induction of water retention, the decrease in the level of red blood cells, the induction of headaches, as well as the risks of hepatotoxicity and cardiac decompensation. These undesirable effects also led to the prohibition in Europe and the withdrawal in the United States in March 2000 of troglitazone (Rezulin®); and, after limiting the indications for rosiglitazone (Avandia®) and pioglitazone (Actos®), to the suspension of their marketing authorization in Europe in 2010 and 2011, respectively.

In this context, the use of medicinal plants appears to be potentially beneficial. In fact, because of their potential action on multiple targets, their use makes it possible to obtain a therapeutic effect while limiting the risk of side effects.

Here, the inventors have identified two species of plants, *Moricandia arvensis* and *Astragalus armatus*, and demonstrated their preventive and curative effects for type 2 diabetes (T2D). These beneficial effects also suggest their potential use in the prevention and/or treatment of other pathologies associated with glycemia deregulation.

*Moricandia arvensis* belongs to the Brassicaceae family and is distributed in the Mediterranean region, particularly in the desert regions of North Africa. This plant, sometimes referred to as "purple mistress" or "violet cabbage", is commonly described for its use in the treatment of syphilis, headaches and scurvy, and exhibits antioxidant and DNA damage protection properties (Skandrani et al., 2010. *Food Chem Toxicol*. 48(2):70-5; Skandrani et al., 2007. *Drug Chem Toxicol*. 30(4):361-82; Braham et al., 2005. *J Nat Prod*. 68(4):517-22).

*Astragalus armatus* belongs to the *Astragalus* genus, which includes 2500 species, and to the Fabaceae family. This plant is found in North Africa, particularly in the Maghreb. *Astragalus armatus* is commonly used in the treatment of colds, asthenia, diarrhea, flu, asthma, and osteoarthritis. The seeds and bark are more specifically used in the treatment of pain, fevers, constipation, snakebites and scorpion bites. This plant also has antioxidant, anti-complement, anticholinesterase, antibacterial and pro-phagocytic properties.

Unexpectedly, the Inventors observed that a treatment with an extract of *Moricandia arvensis* and/or of *Astragalus armatus* prevents hyperglycemia, insulin resistance, glucose intolerance, weight gain and the increase in the fat/lean mass ratio, in a development model of T2D. On the other hand, treatment with an extract of *Moricandia arvensis* and/or of *Astragalus armatus* improves most of these parameters in a pre-clinical model of type 2 diabetes. The Inventors have also demonstrated the fact that *Moricandia arvensis* and *Astragalus armatus* have a protective effect on the secretory capacity of pancreatic cells.

Taken together, these results indicate a novel use of *Moricandia arvensis* and *Astragalus armatus* in the prevention and/or treatment of cardiometabolic diseases, preferably metabolic diseases related to glucose intolerance and/or resistance to insulin.

SUMMARY

The present invention relates to a composition comprising an extract of *Moricandia*, for use in the prevention and/or treatment of a cardiometabolic disease, preferably of a metabolic disease related to glucose intolerance and/or insulin resistance.

In one embodiment, the cardiometabolic disease, preferably the metabolic disease related to glucose intolerance and/or insulin resistance, is selected from the group comprising diabetes, metabolic syndrome, diseases related to insulin resistance or deficiency, glucose intolerance, hyperglycemia, obesity, dyslipidemia, hypercholesterolemia, hypertriglyceridemia, coronary artery disease, cerebrovascular diseases, atherosclerosis, arterial hypertension, oxidative stress, hepatic steatosis and hepatic fibrosis.

In one embodiment, the cardiometabolic disease, preferably the metabolic disease related to glucose intolerance and/or insulin resistance, is selected from the group comprising diabetes, metabolic syndrome, diseases related to insulin resistance or deficiency, glucose intolerance, hyperglycemia, obesity, dyslipidemia, hypercholesterolemia, hypertriglyceridemia and oxidative stress.

In one embodiment, *Moricandia* is *Moricandia arvensis*.

In one embodiment, the extract of Moricandia is a decoction and/or a maceration of *Moricandia*, preferably a decoction and/or a maceration of *Moricandia arvensis*.

In one embodiment, the extract of *Moricandia* is a decoction of *Moricandia* leaves, preferably a decoction of *Moricandia arvensis* leaves, optionally lyophilized.

In one embodiment, the cardiometabolic disease, preferably the metabolic disease related to glucose intolerance and/or insulin resistance, is selected from the group comprising type 2 diabetes, insulin resistance, glucose intolerance and hyperglycemia.

In one embodiment, the cardiometabolic disease, preferably the metabolic disease related to glucose intolerance and/or insulin resistance, is diabetes, preferably type 2 diabetes.

In one embodiment, the composition further comprises an extract of *Astragalus*.

In one embodiment, *Astragalus* is *Astragalus armatus*.

In one embodiment, the extract of *Astragalus* is a decoction and/or maceration of *Astragalus*, preferably a decoction and/or maceration of *Astragalus armatus*.

In one embodiment, the extract of *Astragalus* is a maceration of *Astragalus* roots, preferably a maceration of *Astragalus armatus* roots, preferably a methanolic maceration of *Astragalus armatus* roots, optionally lyophilized.

The present invention also relates to a functional food comprising an extract of *Moricandia*, preferably of *Moricandia arvensis*.

The present invention also relates to a non-therapeutic method for:
 the prevention of weight gain, preferably prevention of fat mass gain in a subject;
 the control of weight gain, preferably the control of fat mass gain in a subject; or
 the stimulation of weight loss, preferably the stimulation of fat mass loss in a subject;
comprising administering to said subject the functional food according to the present invention.

The present invention finally relates to a composition comprising an extract of *Moricandia*, for its use in:
 the prevention of weight gain in a subject, preferably the prevention of fat mass gain in a subject;
 the control of weight gain in a subject, preferably the control of fat mass gain in a subject; or
 the stimulation of weight loss in a subject, preferably the stimulation of fat mass loss in a subject.

In one embodiment, *Moricandia* is *Moricandia arvensis*.

In one embodiment, the extract of *Moricandia* is a decoction and/or maceration of *Moricandia*, preferably a decoction and/or maceration of *Moricandia arvensis*.

In one embodiment, the extract of *Moricandia* is a decoction of *Moricandia* leaves, preferably a decoction of *Moricandia arvensis* leaves, optionally lyophilized.

In one embodiment, the composition further comprises an extract of *Astragalus*, preferably of *Astragalus armatus*, preferably a maceration of *Astragalus armatus* roots, preferably a methanolic maceration of *Astragalus armatus* roots, optionally lyophilized.

In the present invention, the following terms have the following meanings:

The term "*Astragalus*", as used herein, refers to a genus of plants belonging to the Fabaceae family The genus includes over 2 500 different species, which are cataloged and indexed online, for example in the Species 2000 database (Roskov et al., Eds. (2018). *Species 2000 & ITIS Catalog of Life*, 30 Jun. 2018. Digital resource at www.catalogueoflife.org/col. Species 2000: Naturalis, Leiden, the Netherlands. ISSN 2405-8858). A selection of representative species of the *Astragalus* genus includes, but is not limited to, *Astragalus alopecuroides, Astragalus alopecurus, Astragalus alpinus, Astragalus amphioxys, Astragalus armatus, Astragalus australis, Astragalus austriacus, Astragalus baionensis, Astragalagalus boeticus, Astragalus boeticus, Astragalus crenatus, Astragalus frigidus, Astragalus glycyphyllos, Astragalus hamosus, Astragalus hypoglottis, Astragalus lentiginosus, Astragalus membranaceus, Astragalus monspessulanus, Astragalus onobrychis, Astragalus penduliflorus, Astragalus tragalus tragus, Astragalus tragus* and *Astragalus propaginquus*. As used here, however, the term "*Astragalus*" covers all species of *Astragalus* known to date, as well as new species not discovered to date.

The term "*Astragalus armatus*", as used herein, designates a species of plants belonging to the Fabaceae family and mainly distributed in the Maghreb, more particularly in the pre-Saharan areas. The species includes, without being limited to, the following subspecies and varieties: *Astragalus armatus armatus, Astragalus armatus libycus, Astragalus armatus numidicus, Astragalus armatus tragacanthoides* and *Astragalus armatus tumidus*.

The term "atherosclerosis", as used herein, refers to is a disease characterized by the obstruction of the medium- and large-sized arteries (aorta and its branches, coronary arteries, cerebral arteries, arteries of the lower limbs) resulting from the appearance of atheromatous plaques. Atherosclerosis is in particular responsible for coronary artery disease and ischemic cerebrovascular diseases.

The term "consists essentially of", as used herein with reference to a composition, refers to those compositions in which the compound which constitutes them, e.g., an extract, is the only agent having biological activity.

The term "coronary artery disease", also referred to as "coronary insufficiency", as used herein, refers to a group of diseases caused by myocardial ischemia (insufficient supply to the myocardium due to the formation of atheroma in coronary arteries). Coronary artery disease thus includes angina pectoris, myocardial infarction and sudden cardiac death.

The term "decoction", as used herein, refers to an aqueous extraction technique consisting in incubating a plant material in hot water, preferably in boiling water, more preferably while maintaining the boiling for a period of time greater than about 5 minutes, preferably for a period of time greater than 6, 7, 8, 9, 10, 11, 12, 12 or 14 minutes, more preferably for a period of time greater than 15 minutes. In one embodiment, the decoction is made from "fresh" plant material, i.e., not having undergone any prior drying step. In one embodiment, the decoction is made from plant material which is "dry", also defined herein as "dry plant material", i.e., having undergone a prior drying step.

The term "diabetes" as used herein refers to metabolic diseases characterized by a chronic excess of sugar (glucose) in the blood, also referred to as "diabetes mellitus". One of the criteria used to diagnose diabetes is a fasting glycemia level greater than 1.26 g/L of blood (or about 7 mmol/L of blood). There are several types of diabetes:
"type 1 diabetes", also called "juvenile diabetes", is characterized by the disappearance in children or young adults of the β cells of the islets of Langerhans of the pancreas, which produce insulin (autoimmune disease); and
"type 2 diabetes", also called "noninsulin-dependent diabetes", is characterized by the gradual onset of insulin resistance (i.e., when the response of insulin-sensitive cells to insulin is diminished). Insulin resistance is symptomized by the decrease of glucose uptake by fat tissues and muscles and the decrease of hepatic glucose production inhibition. At a more advanced stage, type 2 diabetes can lead to insulin deficiency, i.e., a failure to synthesize insulin by endocrine pancreatic cells.

The term "dyslipidemia", as used herein, refers to a condition, pathological if chronic, in which an abnormally high or, on the contrary an abnormally decreased, quantity of lipids (cholesterol, triglycerides, phospholipids or free fatty acids) circulates in the blood. Dyslipidemia thus groups together on the one hand hyperlipidemia (including more specifically hypercholesterolemia and hypertriglyceridemia) and hypolipidemia (including more specifically hypocholesterolemia).

The term "about", when preceding a numerical value, means plus or minus 10% of said value.

The term "extract", as used herein, refers to a material which has been removed from a plant, or from one or more parts thereof such as, without being limited to, flowers, fruits, seeds, leaves, roots, leaves and/or stem. As is known to those skilled in the art, an extract can either be crude or be refined to a selected degree in order to isolate specified substances or active agents. An extract can be in different forms such as a juice, a decoction, an infusion, a fermentation product, a tincture, an oily macerate, a glycerinated hydroalcoholic macerate, a puree or a powder. Many extraction techniques, known to those skilled in the art, can be used alone or in combination: dehydration, air drying, microwave drying, oven drying, lyophilization, filtration, evaporation, crushing, maceration, percolation, infusion, decoction, Soxhlet extraction, hot continuous extraction, microwave-assisted extraction, ultrasound-assisted extraction, accelerated solvent extraction, extraction by supercritical fluid, aqueous extraction, alcoholic extraction (in particular methanolic or ethanolic), steam distillation, enfleurage, enzymatic digestion and all related techniques.

The term "dry extract", as used herein, refers to the product obtained at the end of an extraction step and in which the extraction solvent has been removed. Techniques for obtaining a dry extract are well known to those skilled in the art, and include, but are not limited to, "lyophilization" and evaporation.

The term "hypercholesterolemia", as used herein, refers to a condition, pathological if chronic, in which an excessive amount of cholesterol circulates in the blood. This amount corresponds to a total cholesterolemia >2.0 g/L before the age of 30 and >2.5 g/L over the age of 30.

The term "hyperglycemia", as used herein, refers to a condition, pathological if chronic, in which an excessive amount of glucose circulates in the blood. According to the Association Française des Diabétiques, this amount corresponds to a glycemia level >1.26 g/L on an empty stomach and >2.00 g/L the rest of the time.

The term "arterial hypertension", as used herein, refers to a condition defined by too high blood pressure. It is commonly referred to as arterial hypertension when systolic blood pressure is >140 mmHg and diastolic blood pressure is >90 mmHg.

The term "hypertriglyceridemia", as used herein, refers to a condition, pathological if chronic, in which an excessive amount of triglycerides circulates in the blood. This amount corresponds to a triglyceridemia >1.5 g/L, or >1.7 mmol/L.

The term "glucose intolerance", sometimes also referred to as "impaired glucose metabolism or tolerance", as used herein, refers to a disease often considered transient to type 2 diabetes. Glucose intolerance can, however, precede the onset of type 2 diabetes for several years. Glucose intolerance is defined by the World Health Organization by a blood glucose level of 6.1 to 6.9 mmol/L on an empty stomach; and/or 7.8 to 11.1 mmol/L two hours after ingesting 75 g of glucose.

The term "lyophilization", as used herein, refers to the removal, by sublimation, of the solvent from a previously frozen composition, thereby providing a "dry extract". The sublimated solvent is usually water, but can also be an alcohol.

The term "maceration", as used herein, denotes a technique consisting in incubating a plant material in a solvent, preferably in a solvent at room or cold temperature (i.e., at about 20-25° C. or less), in order to extract the soluble compounds therefrom. Examples of solvents that can be used for maceration include, but are not limited to, an alcoholic solution (such as, e.g., an ethanol, isopropanol, or methanol solution), water, brine, or an oil.

The term "cerebrovascular diseases", as used herein, refers to a collection of diseases symptomatized by the sudden onset of a neurological deficit due to cerebral damages of vascular origin. In particular, hemorrhagic cerebrovascular diseases are due to the rupture of a blood vessel, while ischemic cerebrovascular diseases are caused by the obstruction of a cerebral artery (see: atherosclerosis).

The terms "diseases related to insulin resistance or deficiency" and "diseases related to glucose intolerance", as used herein, include several metabolic diseases including type 2 diabetes, metabolic syndrome, but also cardiovascular disease (Ford, 2005. *Diabetes Care.* 28(7):1769-78), non-alcoholic fatty liver disease (Bugianesi et al., 2010. *Curr-Pharm Des.* 16(17):1941-51), polycystic ovary syndrome (PCOS) (Diamanti-Kandarakis, 2006. *Endocrine.* 30(1):13-7), Alzheimer's disease (Watson & Craft, 2003. *CNS Drugs.* 17(1):27-45) and cancer (Arcidiacono et al., 2012. *Exp Diabetes Res.* 2012:789174).

The term "plant material", as used herein, refers to the product used for the production of a plant extract useful for the reduction to practice of the present invention. Plant material may consist in a whole plant, with or without its roots, or of one or more parts of a plant, such as, for example, flowers, fruits, seeds, pollen, roots, stems, leaves and/or bark. In one embodiment, the plant material is "fresh", i.e., it has not undergone any preliminary drying step. In one embodiment, the plant material is dry (also defined herein as "dry plant material"), i.e., it has undergone a pre-drying step.

The term "dry plant material", as used herein, denotes a plant material that has undergone a drying step, either naturally (for example, by desiccation in the absence of precipitation in the natural environment of the plant), or by the hand of man by various methods well known to those skilled in the art.

The term "*Moricandia*", as used herein, refers to a genus of plant belonging to the Brassicaceae family The genus includes some forty different species, which are cataloged and indexed online, for example in the Species 2000 database (Roskov et al., Eds. (2018). *Species 2000 & ITIS Catalog of Life*, 30 Jun. 2018. Digital resource at www.catalogueoflife.org/col. Species 2000: Naturalis, Leiden, the Netherlands. ISSN 2405-8858). A selection of representative species of the genus *Moricandia* include, but are not limited to, *Moricandia alypifolia, Moricandia alyssifolia, Moricandia arvensis, Moricandia baetica, Moricandia cinerea, Moricandia clavata, Moricandia crassifolia, Moricandia crenulata, Moricandia divandicandia exacoides, Moricandia divandicandia exacoides, foetida, Moricandia foleyi, Moricandia hesperidiflora, Moricandia longirostris, Moricandia meyeri, Moricandia moricandioides, Moricandia nitens, Moricandia pallida, Moricandia papillosa, Moricandia patula, Moricandia perfoliata, Moricandia sidolia, Morchandia, Morchandia, popchia, Morchandia, popchia, Morchandia, Morchandia, Morchandia, popchia Moricandia suffruticosa, Moricandia teretifolia, Moricandia tortuosa, Moricandia tourneuxii, Moricandia tuberosa* and *Moricandia winkleri*. As used herein, however, the term "*Moricandia*" covers all species of *Moricandia* known to date, as well as new species not discovered to date.

The term "*Moricandia arvensis*", as used herein, refers to a species of plants belonging to the Brassicaceae family and distributed in the Mediterranean region, particularly in the desert regions of northern Africa. The species includes, without being limited to, the following subspecies and varieties: *Moricandia arvensis arvensis, Moricandia arvensis garamantum, Moricandia arvensis nitens, Moricandia arvensis robusta, Moricandia arvensis spinosa* and *Moricandia arvensis suffruticosa*.

The term "obesity", as used herein, refers to a chronic disease (as recognized by the World Health Organization since 1997), defined as an abnormal or excessive accumulation of body fat which can be harmful to health. Still according to the World Health Organization, the definition of obesity is based on the measurement of the body mass index (BMI=mass/height$^2$), classifying the disease into 3 levels: "overweight" if $25$ kg/m$^2$<BMI<$30$ kg/m$^2$; "obesity" if $30$ kg/m$^2$<BMI<$40$ kg/m$^2$; and "morbid obesity" if $40$ kg/m$^2$<BMI.

The term "pharmaceutically acceptable", as used herein, refers to molecules and compositions which do not produce any adverse, allergic or untoward reactions when administered to a subject, in particular to a human. Included are, without limitation, all solvents, dispersing media, coatings, antibacterial and antifungal agents, isotonic agents, absorption-retarding agents and the like. For administration to human, preparations should meet the standards for pyrogenicity, safety and purity required by regulatory agencies, such as the FDA and EMA. A pharmaceutically acceptable vehicle or excipient can thus refer to a solid, semi-solid or liquid encapsulating agent or to an auxiliary formulation of any type.

The term "prediabetic", as used herein, refers to a subject suffering from a medical condition in which their fasting glycemia ranges from about 1 g/L to about 1.26 g/L of blood (i.e., about 5.6 mmol/L to about 7.0 mmol/L of blood), and wherein the risk of developing type 2 diabetes is increased in said subject. A prediabetic subject meeting the above criteria is diagnosed with glucose intolerance.

The term "hepatic steatosis", as used herein, refers to damage to the liver caused by an overload of vacuoles filled with triglycerides accumulating in the cytoplasm of hepatocytes. In particular, "non-alcoholic fatty liver disease", also called "soda illness", is a steatosis unrelated to alcohol intake.

The term "metabolic syndrome", as used herein, refers to a pathological condition preluding more serious metabolic diseases such as type 2 diabetes. According to the National Heart, Lungs and Blood Institute (NHLBI, Bethesda, MD, USA), one talk about "metabolic syndrome" when at least three of the following problems are associated in the same person: abnormally high insulin level, hypercholesterolemia with a low HDL cholesterol level (<1.04 mmol/L for men, <1.29 mmol/L for women), hypertension (>140 mmHg of systolic pressure and/or >90 mmHg of diastolic pressure), excess weight (especially abdominal obesity with a waist circumference >100 cm for men, >88 cm for women), hyperglycemia (blood triglycerides >1.6 mmol/L and/or fasting blood glucose >6.1 mmol/L).

(3A) Graph showing the evolution of glycemia during the test. After 45 min following the insulin injection, while glycemia no longer drops in the HFHS group, the HFHS+MA and AA groups show a glycemia which is not significantly different from the controls and very significantly reduced compared to the untreated HFHS group.
$p<0.01$ and **$p<0.0001$: HFHS vs. HFHS-MA
$p<0.01$ and ####$p<0.0001$: HFHS vs. STD
$p<0.001$ and ####$p<0.0001$: HFHS vs. HFHS-AA
2-way ANOVA test.

(3B) Histogram showing the area under the curves of graph (A). AUC: area under the curve.
**$p<0.01$: HFHS vs. STD
$p<0.05$: HFHS vs. HFHS+MA and HFHS+AA vs. HFHS
2-way ANOVA test.

Figure 1:
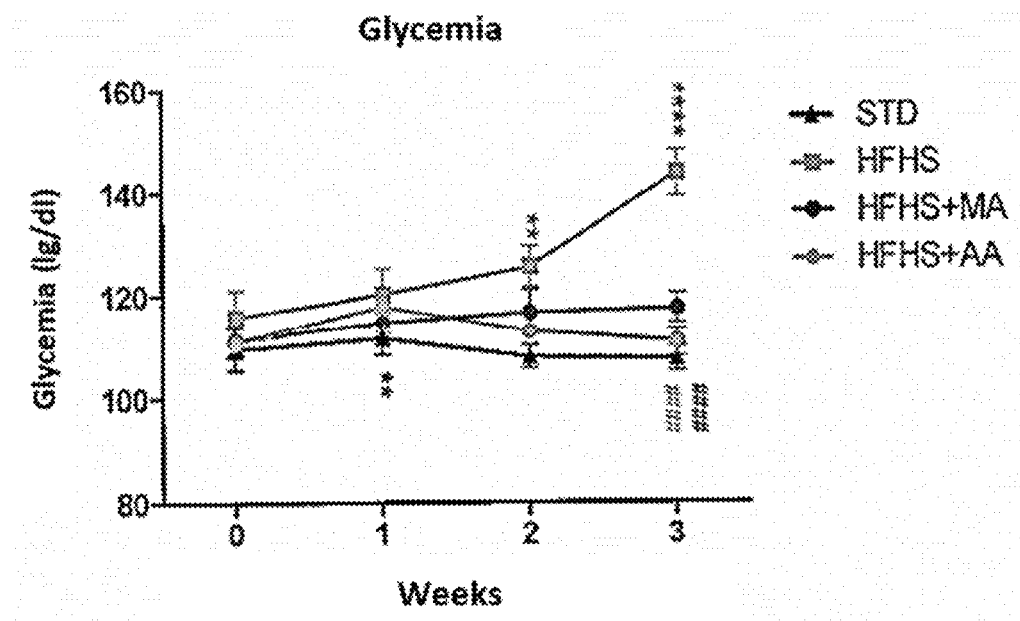
FIG. 1 is a graph showing the evolution of glycemia during the study protocol in the different groups of rats. Glycemia was measured at the start of the protocol and at the end of each of the first three weeks. The legend for the graph reads as follows:
  STD: rats on a standard diet, i.e., reference group;
  HFHS ("High Fat High Sucrose"): rats on a sugar-rich and fat-rich diet, diabetic after 3 weeks;
  HFHS-MA ("High Fat High Sucrose"): rats on a sugar-rich and fat-rich diet, and treated every morning by gavage with 250 mg/kg of an extract of *Moricandia arvensis* from the start of the HFHS diet;
  HFHS-AA ("High Fat High Sucrose"): rats on a sugar-rich and fat-rich diet, and treated every morning by gavage with 250 mg/kg of an extract of *Astragalus armatus* from the start of the HFHS diet.
  *$p<0.01$ and ****$p<0.0001$: STD vs HFHS
  ####$p<0.001$: HFHS vs HFHS+MA and HFHS vs HFHS+AA 2-way ANOVA test.
Figure 4A:
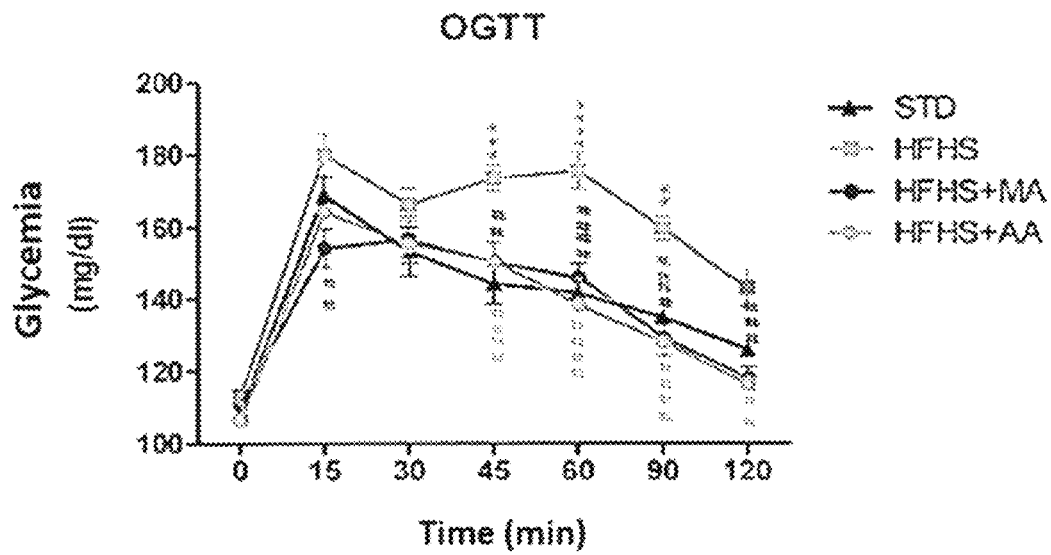
Figure 4B:
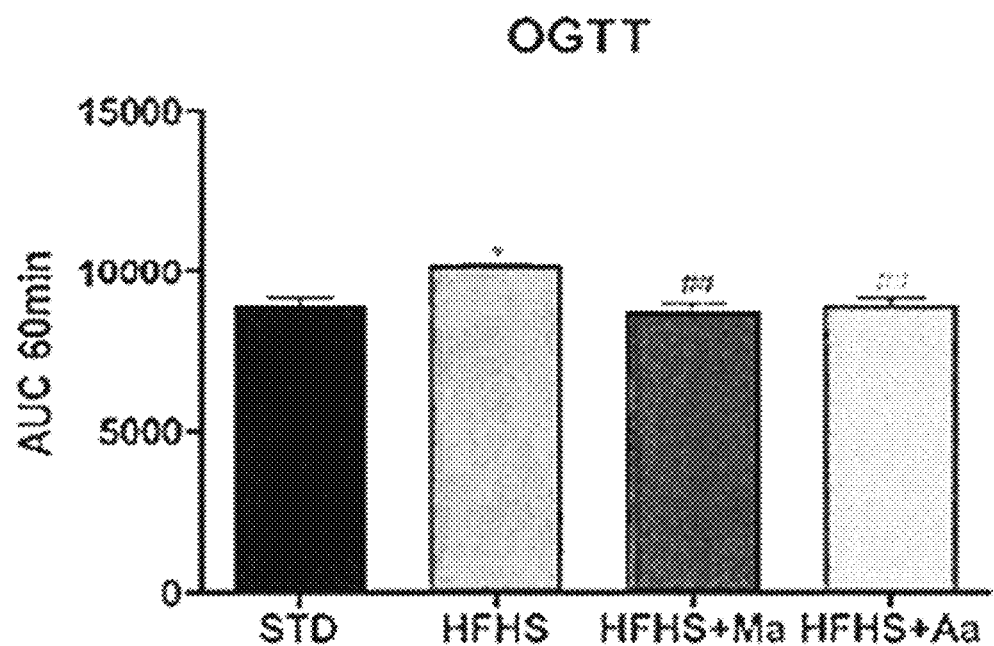
Figure 4C:
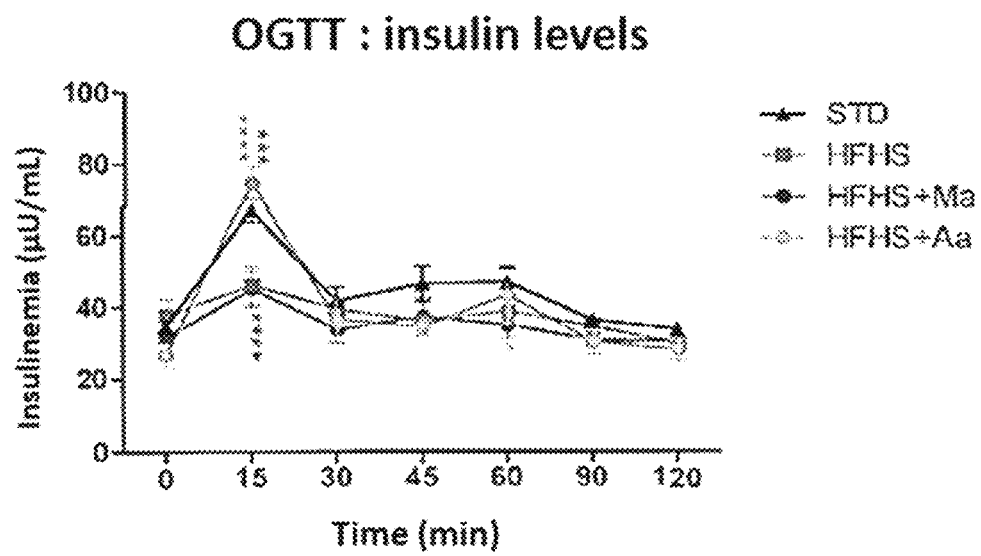

FIGS. 4A, 4B, and 4C shows the results of the glucose tolerance test (2 g/kg orally) carried out at 3 weeks of the study protocol in the different groups of rats as defined in the legend of FIG. 1.

(4A) Graph showing the evolution of glycemia during the test. Animals treated with AA and MA have better glucose tolerance compared to non-treated animals.
$p<0.01$ and *$p<0.001$ and ****$p<0.0001$: HFHS vs. STD
$p<0.01$ and ###$p<0.001$ and ####$p<0.0001$: HFHS-MA vs. HFHS
$p<0.01$ and ####$p<0.0001$: HFHS vs. HFHS-AA
2-way ANOVA test.

(4B) Histogram showing the area under the curve (glycemia as a function of time in the range 0-60 minutes during the test). Glucose intolerance observed in HFHS rats is not present when the HFHS diet was combined with MA or AA treatment.
*$p<0.05$: HFHS vs. STD
$p<0.01$: HFHS-MA vs. HFHS and HFHS vs. HFHS-AA 2-way ANOVA test.

(4C) Graph showing the evolution of insulinemia during the OGTT test. Insulin secretion in response to glucose is impaired in HFHS rats. Insulin secretion in response to glucose remains impaired in HFHS rats treated with MA. In HFHS rats treated with AA, insulin secretion in response to glucose is equivalent to controls.
$p<0.05$: HFHS vs. STD
$p<0.01$: HFHS-MA vs. HFHS and HFHS vs HFHS-AA 2-way ANOVA test.

Figure 5A:
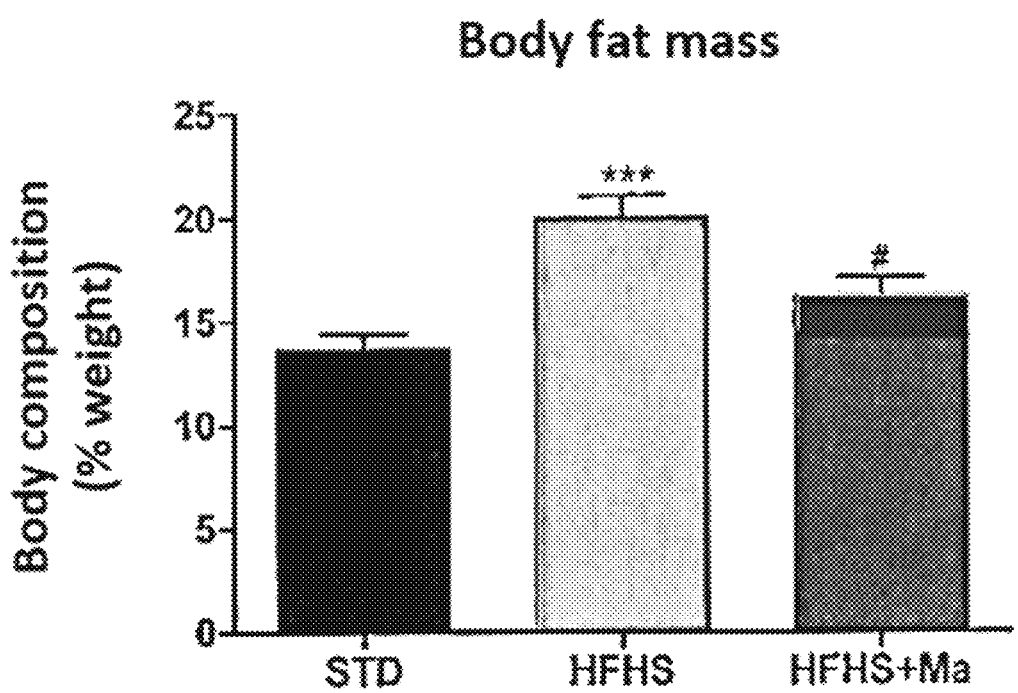
Figure 5B:
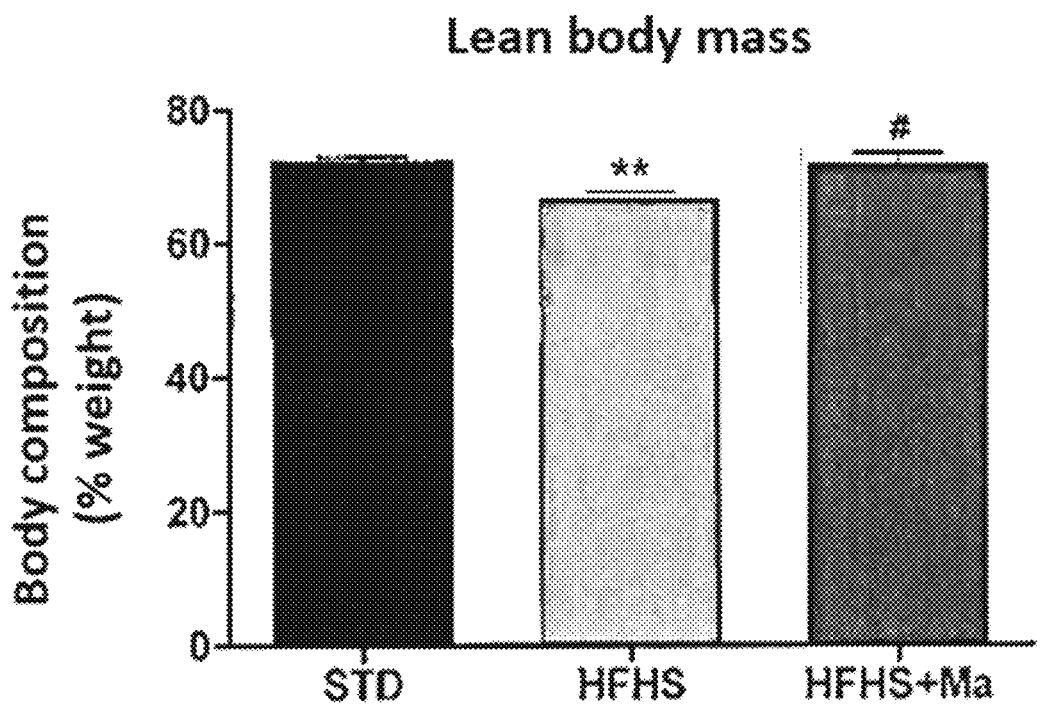

FIGS. 5A and 5B shows the results of the body composition measurement after 3 weeks (1 to 3 days following the 3 weeks of the study protocol) in the different groups of rats.
STD: rats on a standard diet;
HFHS ("High Fat High Sucrose"): rats on a sugar-rich and fat-rich diet;
HFHS-MA ("High Fat High Sucrose"): rats on a sugar-rich and fat-rich diet, and treated every morning by gavage with 250 mg/kg of an extract of *Moricandia arvensis*.

(5A) Histogram illustrating the proportion of fat mass in % of the total weight; % of body water is not shown. The MA treatment helps preventing fat mass gain during the HFHS diet.
***$p<0.001$: HFHS vs. STD
$p<0.05$: HFHS-MA vs HFHS 2-way ANOVA test.

(5B) Histogram illustrating the proportion of lean body mass. The MA treatment helps preventing the lean mass loss during the HFHS diet.
**$p<0.01$: HFHS vs. STD
$p<0.05$: HFHS-MA vs HFHS 2-way ANOVA test.

Figure 6A:
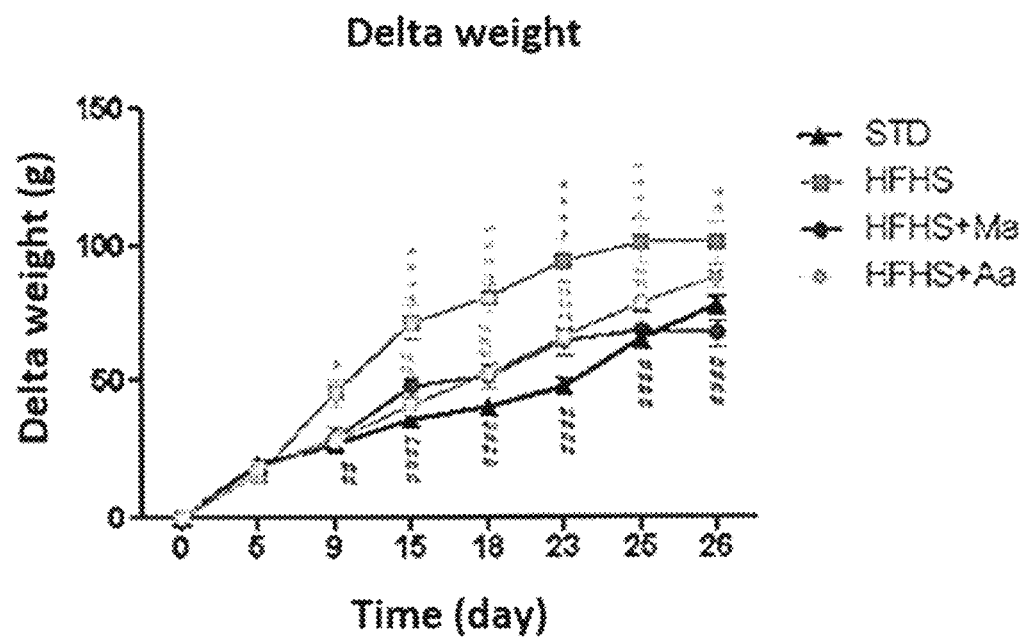
Figure 6B:
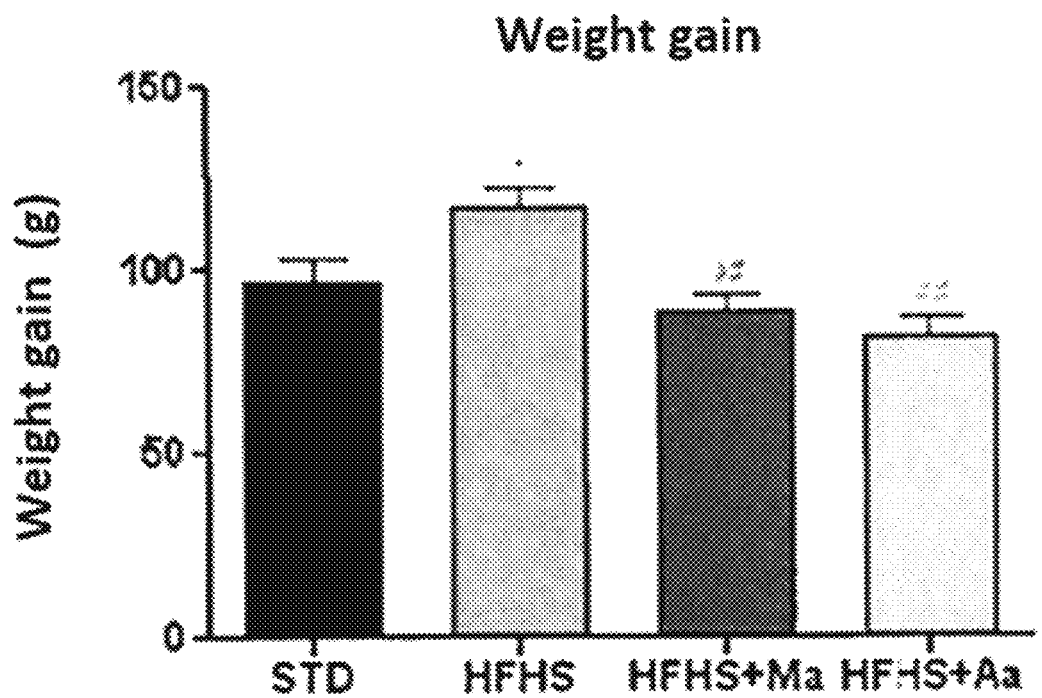

FIGS. 6A and 6B shows the evolution of the differences in weight (delta weight) during the study protocol in the different groups of rats as defined in the legend of the FIG. 1.

(6A) Graph illustrating the change in weight during the study protocol. Animals under the HFHS diet show a greater weight gain than STD control rats. Treatment with MA or AA prevents weight gain in HFHS animals.
*$p<0.05$ and $p<0.01$ and **$p<0.0001$: STD vs. HFHS
$p<0.01$ and ####$p<0.001$: HFHS vs HFHS+MA
$p<0.01$ and ###$p<0.001$: HFHS vs. HFHS+AA 2-way ANOVA test.

(6B) Histogram illustrating weight gain during the study protocol. The HFHS animals treated with MA or AA show an identical weight gain to the STD control rats and significantly lower than the HFHS rats without treatment.
*$p<0.05$ and **$p<0.01$: STD vs. HFHS
$p<0.01$: HFHS vs. HFHS+MA and HFHS vs. HFHS+AA 2-way ANOVA test.

Figure 7:
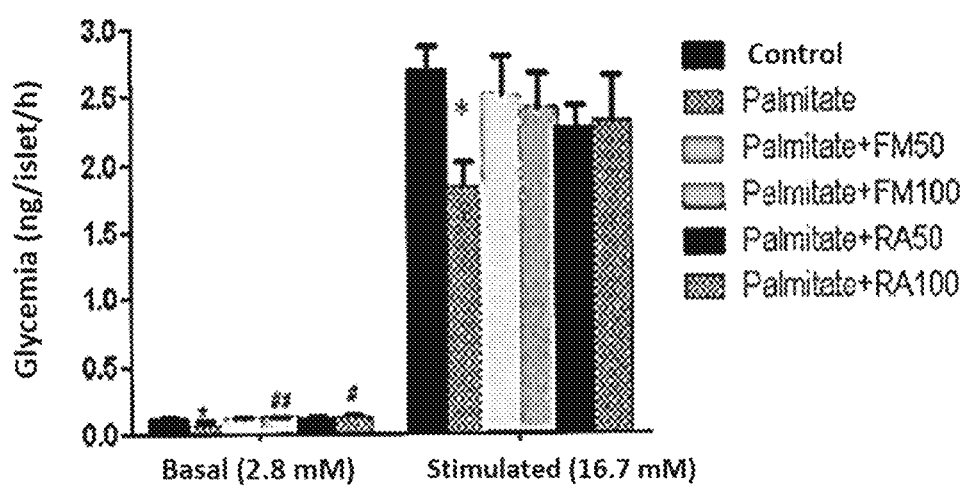

FIG. 7 is a histogram showing the insulin secretion capacity of primary islets of Langerhans from C57Bl6 mice cultured for 72 hours under the following conditions:
control: culture medium alone;
palmitate: culture medium+0.5 mM palmitate (lipotoxic conditions mimicking the environment of T2D);
palmitate+FM50 (*M. arvensis* 50 mg): culture medium+0.5 mM palmitate+50 µg/mL of *Moricandia arvensis* leaf extract;
palmitate+FM100 (*M. arvensis* 100 mg): culture medium+0.5 mM palmitate+100 µg/mL of *Moricandia arvensis* leaf extract;
palmitate+RA50 (*A. armatus* 50 mg): culture medium+0.5 mM palmitate+50 µg/mL of *Astragalus armatus* root extract;
palmitate+RA100 (*A. armatus* 100 mg): culture medium+0.5 mM palmitate+100 µg/mL of *Astragalus armatus* root extract.

Insulin secretion was measured in vitro either under basal conditions (non-stimulating glucose concentration: 2.8 mM) or after stimulation (16.7 mM glucose) at the end of the predefined culture conditions. Treatment with an extract of *Moricandia arvensis* or of *Astragalus armatus* in "palmitate" condition restores insulin secretion similar to that of islets in normal condition.
*$p<0.05$: control vs. palmitate
$p<0.01$: palmitate vs. P+FM100
$p<0.05$: palmitate vs. P+RA100

Figure 8:
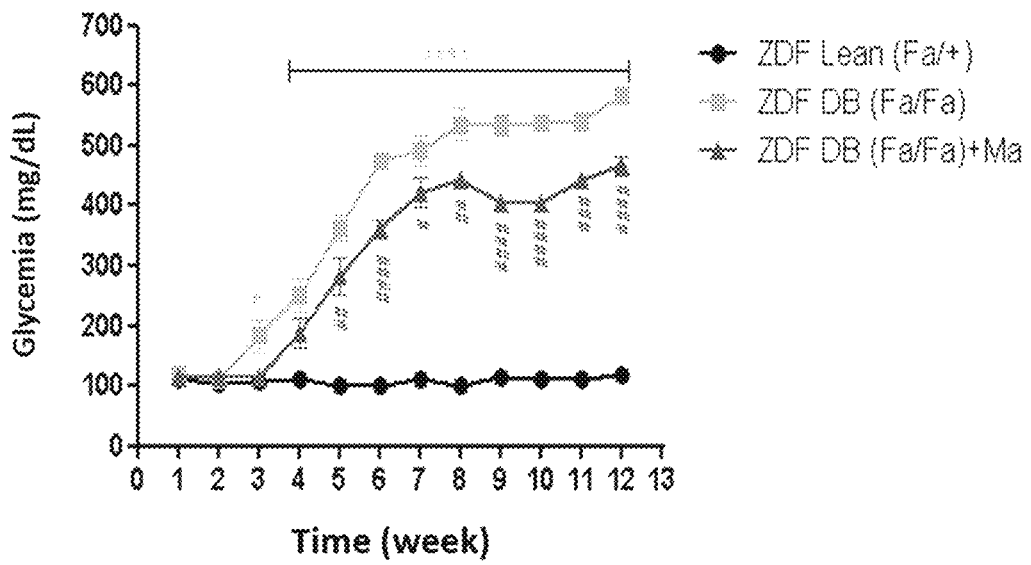

FIG. 8 is a graph showing the evolution of glycemia during the study protocol in the different groups of ZDF rats. Follow-up is done at the end of each week for 12 weeks.
ZDF Lean (fa/+): control, heterozygous for the recessive mutation or homozygous for the wild-type leptin receptor allele, i.e., reference group.

ZDF DB (fa/fa): homozygous for the leptin receptor mutation. The animals are obese, insulin-resistant and then irreversibly diabetic.

ZDF DB (fa/fa)+MA: homozygous for the mutation of the leptin receptor, treated by gavage with 250 mg/kg of a *Moricandia arvensis* extract prepared as described in FIG. 1 above.

*p<0.05 and ****p<0.001: ZDF DB vs. ZDF lean
p<0.05 and ##p<0.01 and ###p<0.001 and ####p<0.0001: ZDF DB+MA vs. ZDF DB
Two-way ANOVA test.

Figure 9:
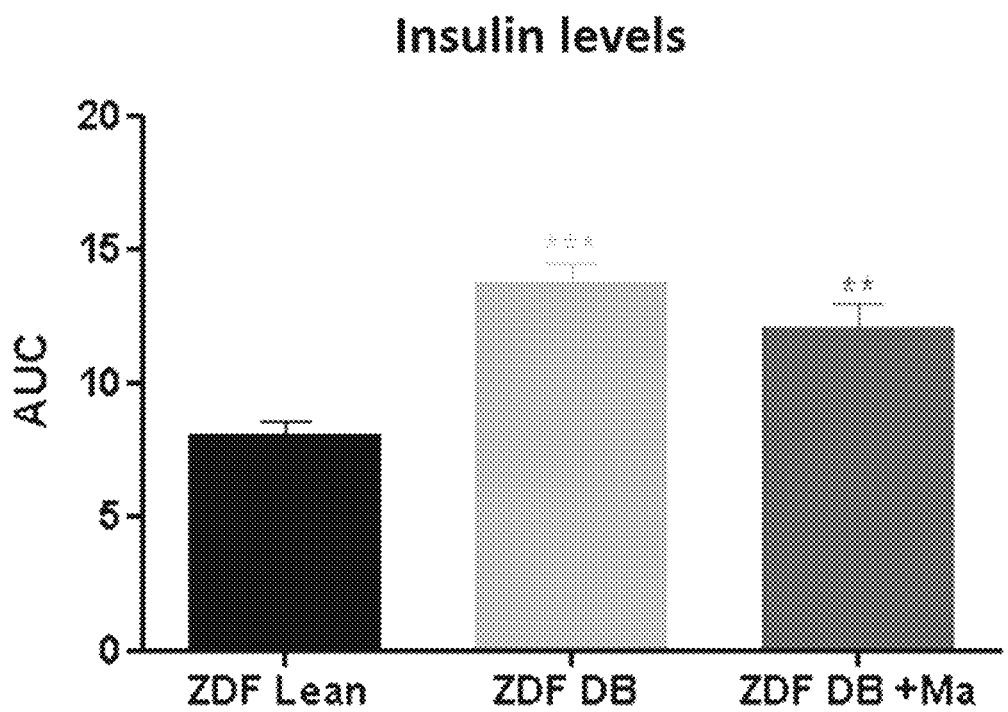

FIG. 9 is a histogram showing the evolution of insulinemia over time (integration of the area under the curve) during the first 8 weeks of the study protocol in the different groups of rats as defined in the legend of the FIG. 8.

p<0.01 and *p<0.001: ZDF DB vs. ZDF lean
Two-way ANOVA test.

FIG. 10 shows the results of the insulin sensitivity test (1 U/kg) carried out after 8 weeks of the study protocol in the different groups of rats as defined in the legend of FIG. 8.

(10A) Graph showing the evolution of glycemia during the test. Both groups of ZDF DB and ZDF DB+MA diabetic rats were hyperglycemic compared to the ZDF lean control group during the first 45 minutes following insulin injection. The untreated ZDF DB group is insulin-resistant throughout the test compared to the control ZDF group, whereas in the group treated with MA (ZDF DB+MA), insulin resistance gradually disappears (significant improvement after 60 minutes, to become insignificant compared to the ZDF lean control group). In the interval between 75 and 120 minutes, insulin sensitivity becomes identical between the ZDF DB+MA and ZDF lean groups, thus allowing a complete restoration of glycemia in response to exogenous insulin.

****p<0.001: ZDF DB vs. ZDF lean
p<0.01 and **p<0.001: ZDF DB+MA vs. ZDF lean
Two-way ANOVA test.

(10B) Area under the curve integrating glycemia during the first 60 minutes of the test.

ZDF DB+MA rats have a lower glycemic excursion than untreated ZDF DB rats but higher than ZDF lean rats.

**p<0.01: ZDF DB+MA vs. ZDF lean
****p<0.0001: ZDF DB vs. ZDF lean
p<0.01: ZDF DB+MA vs. ZDF DB
Two-way ANOVA test.

Figure 11A:
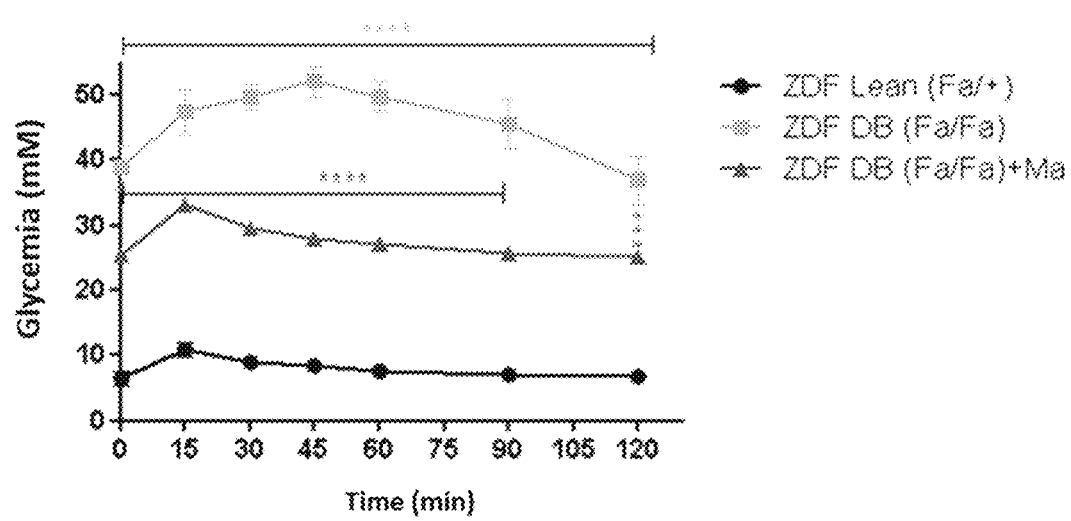
Figure 11B:
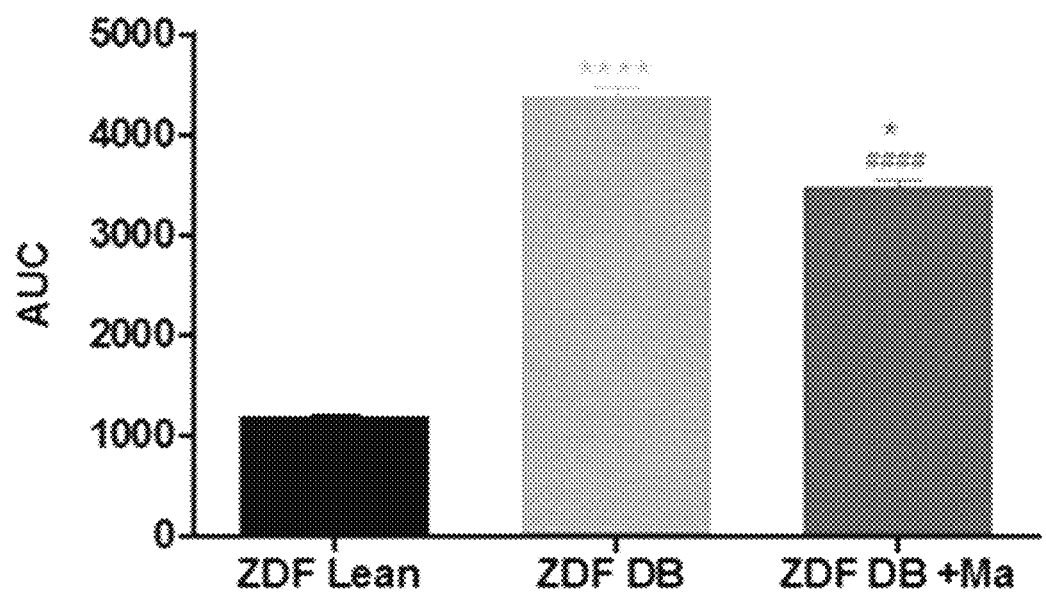

FIGS. 11A and 11B shows the results of the glucose tolerance test (2 g/kg) carried out after 8 weeks of the study protocol in the different groups of rats as defined in the legend of FIG. 8.

(11A) Graph showing the evolution of glycemia during the test. Glycemia is significantly higher in ZDF DB rats than in ZDF+MA rats.

p<0.01 and **p<0.001: ZDF DB+MA vs. ZDF DB
***p<0.001: ZDF DB vs. ZDF lean
Two-way ANOVA test.

(11B) Histograms illustrating the area under the glycemia trend curves as a function of time in the range 0-60 minutes during the test.

*p<0.05: ZDF DB+MA vs. ZDF-DB
****p<0.001: ZDF DB vs. ZDF lean
p<0.001: ZDF DB+MA vs. ZDF lean
Two-way ANOVA test.

Figure 12:
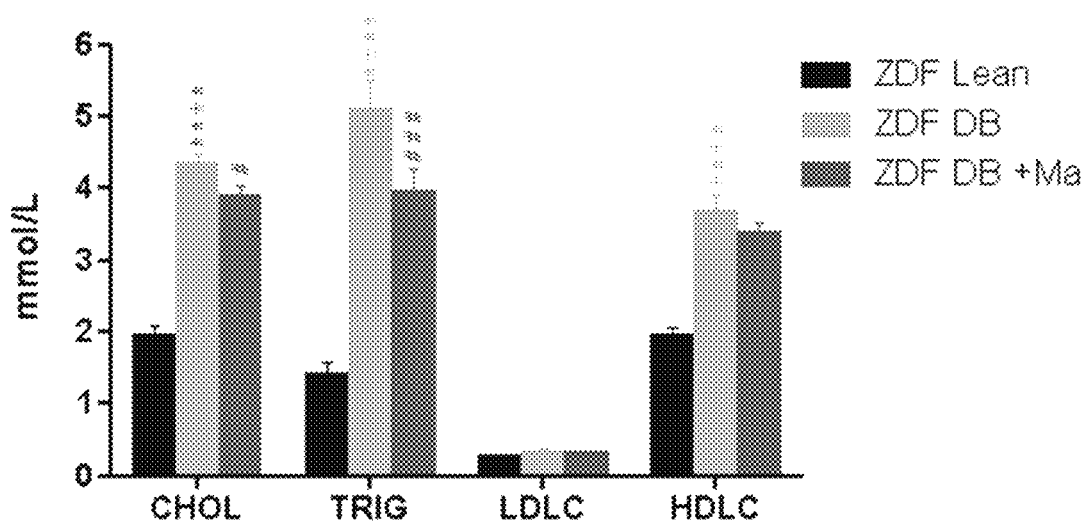

FIG. 12 shows in histogram form the lipid balance (total cholesterol and triglycerides) in the 3 groups of rats as defined in the legend of FIG. 8. The levels of total cholesterol (CHOL), triglycerides (TRIG), low density lipoprotein cholesterol (LDLC) and high-density lipoprotein cholesterol (HDLC) are indicated.

****p<0.0001: ZDF DB vs. ZDF lean
p<0.05 and ###p<0.001: ZDF DB+MA vs. ZDF DB
Two-way ANOVA test.

DETAILED DESCRIPTION

The present invention relates to a composition comprising at least one extract of *Moricandia* for use in the prevention and/or treatment of cardiometabolic diseases, preferably of a metabolic disease related to glucose intolerance and/or insulin resistance.

In one embodiment, the composition according to the present invention comprises, consists of, or consists essentially of, at least one extract of *Moricandia*.

According to one embodiment, the at least one extract of *Moricandia* is an extract of a species of *Moricandia* selected from the group comprising or consisting of *Moricandia alypifolia*, *Moricandia alyssifolia*, *Moricandia arvensis*, *Moricandia baetica*, *Moricandia cinerea*, *Moricandia clavata*, *Moricandia crassifolia*, *Moricandia crenulata*, *Moricandia divaricata*, *Moricandia dumosa*, *Moricandia exacoides*, *Moricandia foetida*, *Moricandia foleyi*, *Moricandia hesperidiflora*, *Moricandia longirostris*, *Moricandia meyeri*, *Moricandia moricandioides*, *Moricandia pallosa*, *Moricandia pallosa*, *Moricandia pallosa*, *Moricandia pallosa*, *Moricandia patillia*, *Moricandioides*, *Moricandia pallosa*, *Moricandia pallosa*, *Moricandia pallosa*, *Moricandia patina*, *Moricandia pallosa*, *Moricandia patillia*, *Moricandia ramburii*, *Moricandia sinaica*, *Moricandia sonchifolia*, *Moricandia sonchifolia*, *Moricandia spinosa*, *Moricandia seffreticosa*, *Moricandia teretifolia*, *Moricandia tortuosa*, *Moricandia tourneuxii*, *Moricandia tuberosa*, and *Moricandia winkleri*.

According to a preferred embodiment, the at least one extract of *Moricandia* is an extract of *Moricandia arvensis*.

In one embodiment, the composition according to the present invention further comprises at least one extract of *Astragalus*.

According to one embodiment, the at least one extract of *Astragalus* is an extract of a species of *Astragalus* selected from the group comprising or consisting of *Astragalus alopecuroides*, *Astragales alopeceres*, *Alpine astragalus*, *Astragalus amphioxys*, *Astragalus armates*, *Astragales aestralis*, *Astragales aestriaces*, *Astragales baionensis*, *Astragales boetices*, *Astragales cicer*, *Astragalus crassicarpes*, *Astragales crenatus*, *Astragalus frigidus*, *Astragalus glycyphyllos*, *Astragalus hamosus*, *Astragalus hypoglottis*, *Astragalus lentiginosus*, *Astragalus onus mulcinobryus*, *Astragalus onus mulcinobryus*, *Astragalus onus mulcinobryus*, *Astragalus onus mulcinobryus*, *Astragalus onus mulipinobryus*, *Astragalus onus mulcinobryus*, *Astragalus onus mulcinobry* and *Astragalus tragacantha*.

According to a preferred embodiment, the at least one extract of *Astragalus* is an extract of *Astragalus armatus*.

In one embodiment, the "at least one extract" can be obtained by any extraction method comprising one (or a combination of) technique(s) known to those skilled in the art. Examples of extraction techniques include, but are not limited to, dehydration, air drying, microwave drying, oven drying, lyophilization, filtration, grinding, maceration, percolation, infusion, decoction, Soxhlet extraction, hot continuous extraction, microwave-assisted extraction, ultrasound-assisted extraction, accelerated solvent extraction, extraction by supercritical fluid, aqueous extraction, alcoholic extraction (in particular methanolic or ethanolic), steam distillation, enfleurage, enzymatic digestion and all related techniques.

In one embodiment, the "at least one extract" can be obtained from a starting plant material comprising or consisting of the whole plant (i.e., a plant of the *Moricandia* genus, preferably *Moricandia arvensis*; and/or a plant of the *Astragalus* genus, preferably *Astragalus armatus*).

In one embodiment, the "at least one extract" can be obtained from a starting plant material comprising or consisting of one or more parts of the plant. Examples of plant parts which can be used to produce an extract include, but are not limited to, flowers, fruits, seeds, pollen, roots, stems, leaves and bark.

In a preferred embodiment, the "at least one extract of *Moricandia*, preferably of *Moricandia arvensis*" is a leaf extract.

In a preferred embodiment, the "at least one extract of *Astragalus*, preferably of *Astragalus armatus*" is a root extract.

In one embodiment, the plant material is dried after harvesting.

In one embodiment, the plant material is air-dried and protected from the sun.

In one embodiment, the plant material is air-dried and protected from the sun for a period of time ranging from about 7 days to 25 days, preferably from about 10 days to 20 days, more preferably for a period of time of about 14 days.

In one embodiment, the plant material is air-dried and protected from the sun for a period of time of at least about 7 days, preferably at least about 7, 8, 9, 10, 11, 12, 13 days, more preferably for a period of time of at least about 14 days.

In one embodiment, the "at least one extract" can be obtained by a method comprising a decoction step.

In a preferred embodiment, the "at least one extract of *Moricandia*, preferably of *Moricandia arvensis*" can be obtained by a method comprising a decoction step.

In one embodiment, the duration of the decoction step ranges from about 5 minutes to about 30 minutes, preferably from about 10 minutes to about 25 minutes, more preferably from about 15 to about 20 minutes. In one embodiment, the duration of the decoction step is greater than about 5 minutes, preferably about 6, 7, 8, 9, 10, 11, 12, 13 or 14 minutes, more preferably about 15 minutes.

In one embodiment, the decoction temperature is greater than about 40° C., preferably greater than about 45° C., 50° C., 55° C., 60° C., 65° C., 70° C., 75° C., 80° C. or 85° C., more preferably greater than about 90° C. In a preferred embodiment, the decoction temperature is about 100° C.

In one embodiment in which the decoction is made from a dry plant material, the mass of dry plant material per volume of water for the decoction ranges from about 1 g/L to about 200 g/L, preferably from about 50 g/L to 150 g/L, more preferably the mass of dry plant material per volume of water for the decoction is about 100 g/L. In one embodiment in which the decoction is made from dry plant material, the mass of dry plant material per volume of water for the decoction is greater than about 1 g/L, preferably greater than about 10 g/L, more preferably greater than about 20 g/L, 30 g/L, 40 g/L, 50 g/L, 60 g/L, 70 g/L or 80 g/L. In a preferred embodiment in which the decoction is made from dry plant material, the mass of dry plant material per volume of water for the decoction is greater than about 90 g/L.

In a preferred embodiment, the "at least one extract of *Moricandia*, preferably of *Moricandia arvensis*" can be obtained by a method comprising a step of decoction of leaves of *Moricandia*, preferably of *Moricandia arvensis*.

In one embodiment, the "at least one extract" can be obtained by a method comprising a maceration step.

In one embodiment, the "at least one extract" can be obtained by a method comprising a step of maceration in a solution of methanol.

In a preferred embodiment, the "at least one extract of *Astragalus*, preferably of *Astragales armatus*", can be obtained by a method comprising a maceration step, preferably an alcoholic maceration step (i.e., in a solvent. comprising an alcoholic solution), more preferably a methanolic maceration step (i.e., in a solvent comprising a methanol solution).

In one embodiment, the duration of the maceration step ranges from about 1 day to about 30 days, preferably from about 5 days to about 25 days, more preferably from about 10 days to about 20 days. In one embodiment, the duration of the maceration step is greater than 2 days, preferably greater than 3, 4, 5, 6, 7, 8, 9, 10, 11, 12 or 13 days, more preferably the duration of the maceration step is greater than 14 days. In a preferred embodiment, the duration of the maceration step is about 15 days.

In one embodiment, the maceration step is carried out without stirring. In a preferred embodiment, the maceration step is carried out with stirring.

In one embodiment in which the maceration is carried out from a dry plant material, the mass of dry plant material per volume of solvent for the maceration ranges from about 1 g/L to about 200 g/L, preferably from about 50 g/L to about 150 g/L, more preferably the mass of dry plant material per volume of solvent for the maceration is about 100 g/L. In one embodiment in which the maceration is carried out from a dry plant material, the mass of dry plant material per volume of solvent for the maceration is greater than 1 g/L, preferably greater than 10 g/L, more preferably greater than 20 g/L, 30 g/L, 40 g/L, 50 g/L, 60 g/L, 70 g/L, 80 g/L or 90 g/L.

In a preferred embodiment, the "at least one extract of *Astragalus*, preferably of *Astragalus armatus*", can be obtained by a method comprising a step of maceration of roots of *Astragalus*, preferably of *Astragalus armatus*, preferably a step of alcoholic maceration of *Astragalus* roots, preferably of *Astragalus armatus*, more preferably a step of methanolic maceration of *Astragalus* roots, preferably of *Astragalus armatus*.

In one embodiment, the "at least one extract" can be obtained by a method comprising a lyophilization step.

In one embodiment, the "at least one extract" can be obtained by a method comprising a filtration step.

In one embodiment, the "at least one extract" can be obtained by a method comprising an evaporation step.

In a preferred embodiment, the "at least one extract of *Astragalus*, preferably of *Astragalus armatus*", can be obtained by a method comprising an evaporation step, preferably an evaporation step under reduced pressure at 40° C.

In one embodiment, the "at least one extract" is a dry extract.

In one embodiment, the "at least one extract" can be stored at a temperature ranging from about −196° C. to about +40° C., preferably from about −80° C. to about +30° C., preferably from about −20° C. to about +25° C., preferably at a temperature of about +4° C.

In one embodiment, the composition according to the present invention is a pharmaceutical composition or a medicament.

The present invention therefore also relates to a pharmaceutical composition comprising, consisting of or consisting essentially of the composition according to the present invention and at least one pharmaceutically acceptable excipient.

Examples of a pharmaceutically acceptable excipients include, but are not limited to, surfactants, binders, diluents, lubricants, preservatives, stabilizers, antioxidants, suspensions, delivery systems, ion exchangers, alumina, aluminum stearate, lecithin, serum proteins, such as human serum albumin, buffering substances such as phosphates, glycine, sorbic acid, potassium sorbate, saturated vegetable fatty acids partial glyceride mixtures, water, salts or electrolytes, such as protamine sulfate, sodium hydrogen phosphate, potassium hydrogen phosphate, sodium chloride, zinc salts, silica, colloidal silica, magnesium trisilicate, polyvinylpyrrolidone, cellulose-based substances (e.g., sodium carboxymethylcellulose), polyethylene glycol, polyacrylates, waxes and lanolin.

The present invention therefore also relates to a medicament comprising, consisting of or consisting essentially of the composition according to the present invention.

In one embodiment, the composition according to the present invention is a nutraceutical or food composition. Such a composition is also known under the term of "functional food", i.e., a food whose formulation involves an active effect on the health and/or well-being of the subject taking it.

The present invention therefore also relates to a nutraceutical or food composition comprising, consisting of or consisting essentially of the composition according to the invention.

In one embodiment, the present invention relates to the composition, pharmaceutical composition, nutraceutical composition or medicament as described above, for use in the prevention and/or treatment of cardiometabolic diseases, preferably of a metabolic disease related to glucose intolerance and/or insulin resistance.

In one embodiment, the present invention relates to the use of the composition, pharmaceutical composition, nutraceutical composition or medicament as described above, in the manufacture of a medicament for the prevention and/or treatment of cardiometabolic diseases, preferably of a metabolic disease related to glucose intolerance and/or insulin resistance.

In one embodiment, the present invention relates to a method of preventing and/or treating a cardiometabolic disease, preferably a metabolic disease related to glucose intolerance and/or insulin resistance, in a subject, comprising administering the composition, pharmaceutical composition, nutraceutical composition or medicament as described above.

Examples of cardiometabolic diseases include, but are not limited to, diabetes (e.g., type 2 diabetes or type 1 diabetes), metabolic syndrome, diseases related to insulin resistance or deficiency, glucose intolerance, hyperglycemia, obesity, dyslipidemia, hypercholesterolemia, hypertriglyceridemia, coronary artery disease, cerebrovascular diseases, atherosclerosis, arterial hypertension, oxidative stress, hepatic steatosis (in particular, non-alcoholic fatty liver disease) and hepatic fibrosis.

Examples of metabolic diseases related to glucose intolerance and/or insulin resistance include, but are not limited to, diabetes (e.g., type 2 diabetes or type 1 diabetes), metabolic syndrome, diseases related to insulin resistance or deficiency, glucose intolerance, hyperglycemia, obesity, dyslipidemia, hypercholesterolemia, hypertriglyceridemia and oxidative stress.

According to a preferred embodiment, the cardiometabolic disease, preferably the metabolic disease related to glucose intolerance and/or insulin resistance, is selected from type 2 diabetes, insulin resistance, glucose intolerance and hyperglycemia.

According to a preferred embodiment, the cardiometabolic disease, preferably the metabolic disease related to glucose intolerance and/or insulin resistance, is diabetes. According to a preferred embodiment, the cardiometabolic disease, preferably the metabolic disease related to glucose intolerance and/or insulin resistance, is type 2 diabetes.

In one embodiment, the present invention relates to the composition, pharmaceutical composition, nutraceutical composition or medicament as described above, for use in a method of increasing glucose tolerance in a subject. In one embodiment, the present invention relates to a method of increasing glucose tolerance in a subject, comprising administering the composition, pharmaceutical composition, nutraceutical composition, or medicament as described above.

Techniques for assessing glucose tolerance in a subject are well known to those skilled in the art. For example, glucose tolerance can be assessed by a glucose tolerance test, as will be described in the Examples section below.

In one embodiment, the present invention relates to the composition, pharmaceutical composition, nutraceutical composition or medicament as described above, for use in reducing the increase in the proportion of body fat mass in a subject. In one embodiment, the present invention relates to a method of reducing the increase in the proportion of body fat mass in a subject, comprising administering the composition, pharmaceutical composition, nutraceutical composition or medicament as described above.

In one embodiment, the present invention relates to the composition, pharmaceutical composition, nutraceutical composition or medicament as described above, for use in reducing the decrease in the proportion of lean body mass in a subject. In one embodiment, the present invention relates to a method of reducing the decrease in the proportion of lean body mass in a subject, comprising administering the composition, pharmaceutical composition, nutraceutical composition or medicament as described above.

The techniques for measuring the proportion of fat mass and/or lean mass in a subject are known to those skilled in the art. For example, body composition can be measured by magnetic resonance imaging, as will be described in the Examples section below.

In one embodiment, the present invention relates to the composition, pharmaceutical composition, nutraceutical composition or medicament as described above, for use in increasing insulin secretion in a subject. In one embodiment, the present invention relates to a method of increasing insulin secretion in a subject, comprising administering the composition, pharmaceutical composition, nutraceutical composition or medicament as described above.

Techniques for measuring insulin secretion in a subject are well known to those skilled in the art. For example, insulinemia (basal or after oral-induced hyperglycemia) can be measured to determine the level of insulin secreted in the subject, as will be described in the Examples section below.

In one embodiment, the present invention relates to the composition, pharmaceutical composition, nutraceutical composition or medicament as described above, for use in normalizing glycemia levels in a subject. In one embodiment, the present invention relates to a method of normalizing glycemia levels in a subject, comprising administering the composition, pharmaceutical composition, nutraceutical composition or medicament as described above.

The term "normalization of glycemia" is understood to mean the return of the glucose concentration measured in the blood of the subject to a level ranging from about 0.5 g/L to about 1.26 g/L, preferably from about 0.7 g/L to about 1.10 g/L, preferably from about 0.7 g/L to about 1.0 g/L.

In one embodiment, the present invention relates to the composition, pharmaceutical composition, nutraceutical composition or medicament as described above, for use in preventing weight gain in a subject. In one embodiment, the present invention relates to a method of preventing weight gain in a subject, comprising administering the composition, pharmaceutical composition, nutraceutical composition or medicament as described above.

In one embodiment, the present invention relates to the composition, the pharmaceutical composition, the nutraceutical composition or the medicament as described above, for use in the prevention of fat mass gain in a subject. In one embodiment, the present invention relates to a method of preventing fat mass gain in a subject, comprising administering the composition, pharmaceutical composition, nutraceutical composition or medicament as described above.

In one embodiment, the present invention relates to the composition, pharmaceutical composition, nutraceutical composition or medicament as described above, for use in controlling weight gain in a subject. In one embodiment, the present invention relates to a method of controlling weight gain in a subject, comprising administering the composition, pharmaceutical composition, nutraceutical composition or medicament as described above.

In one embodiment, the present invention relates to the composition, the pharmaceutical composition, the nutraceutical composition or the medicament as described above, for use in the control of fat mass gain in a subject. In one embodiment, the present invention relates to a method of controlling fat mass gain in a subject, comprising administering the composition, the pharmaceutical composition, the nutraceutical composition or the medicament as described above.

In one embodiment, the present invention relates to the composition, pharmaceutical composition, nutraceutical composition or medicament as described above, for use in stimulating weight loss in a subject. In one embodiment, the present invention relates to a method of stimulating weight loss in a subject, comprising administering the composition, pharmaceutical composition, nutraceutical composition or medicament as described above.

In one embodiment, the present invention relates to the composition, pharmaceutical composition, nutraceutical composition or medicament as described above, for use in stimulating fat mass loss in a subject. In one embodiment, the present invention relates to a method of stimulating fat mass loss in a subject, comprising administering the composition, pharmaceutical composition, nutraceutical composition or medicament as described above.

In one embodiment, the present invention relates to a cosmetic (or non-therapeutic) method comprising administering the composition or the nutraceutical composition according to the invention.

In one embodiment, the cosmetic or non-therapeutic method according to the present invention is intended to prevent weight gain in a subject. In one embodiment, the cosmetic or non-therapeutic method according to the present invention is intended to prevent fat mass gain in a subject.

In one embodiment, the cosmetic or non-therapeutic method according to the present invention is intended to control weight gain in a subject. In one embodiment, the cosmetic or non-therapeutic method according to the present invention is intended to control fat mass gain in a subject.

In one embodiment, the cosmetic or non-therapeutic method according to the present invention is intended to stimulate weight loss in a subject. In one embodiment, the cosmetic or non-therapeutic method according to the present invention is intended to stimulate fat mass loss in a subject.

In a preferred embodiment, the cosmetic (or non-therapeutic) methods according to the present invention are intended for substantially healthy subjects. By "substantially healthy" is meant a subject who is not affected, and/or has not been diagnosed, with a cardiometabolic disease, preferably with a metabolic disease related to glucose intolerance and/or insulin resistance, as defined above.

In one embodiment, the composition, pharmaceutical composition, nutraceutical composition or medicament according to the invention is administered systemically or locally.

In one embodiment, the composition, pharmaceutical composition, nutraceutical composition or medicament according to the invention is administered orally, buccally, by injection, percutaneously, parenterally, intraperitoneally, rectally, vaginally, topically, transdermally or transmucosally, nasally, by inhalation or through the use of an implanted reservoir.

In one embodiment, the composition, pharmaceutical composition, nutraceutical composition or medicament according to the invention is administered orally.

In this context, various galenical forms are possible, such as in particular solid, semi-solid, flexible, liquid, vaporized or pressurized forms, vaporizations and ultrasonic diffusions.

Examples of solid forms suitable for oral administration include, but are not limited to, pills, lozenges, granules, powders, gums or chewing gums, soft-shell capsules, hard capsules, cachets, coated or uncoated tablets, effervescent tablets, modified-release tablets, orodispersible or gastro-resistant tablets, dragees and other solid forms suitable for preparing a solution or suspension before oral administration, such as oral powders, lyophilized powders soluble in a hot or cold liquid.

Examples of liquid forms suitable for oral administration include, but are not limited to, syrups, emulsions, solutions, suspensions, infusions, herbal teas, mother tinctures, officinal tinctures, macerates, oily macerates, vegetable oils, glycerinated hydroalcoholic macerates, decoctions, nebulizers and sprays.

Examples of pressurized or pneumatic dosage forms include, but are not limited to, nebulizers, inhalers and sonic diffusers.

In one embodiment, the composition, the pharmaceutical composition, the nutraceutical composition or the medicament according to the invention, more preferably the nutraceutical composition, can also be provided in the form of a food supplement or food additive. Examples of such supplements or additives include, but are not limited to, solid supplements (such as shreds and kibbles of dried or fresh plants or of a dried or fresh plant part, powders to be diluted or mixed with food, food bars, etc.) and liquid supplements (such as beverages, syrups, emulsions, solutions, infusions, herbal teas, mother tinctures, macerates, oily macerates, glycerinated hydroalcoholic macerates and other decoctions). The term beverage as used herein includes, but is not limited to, alcoholic beverages, non-alcoholic beverages, teas, infusions, herbal teas, concoctions, energy drinks, fruit juices, lemonades, sodas, dairy products, soups. In the case of liquid supplements more specifically, these can come in various forms such as ready-to-consume supplements or concentrates to be diluted.

In one embodiment, the composition, the pharmaceutical composition, the nutraceutical composition or the medicament according to the invention is administered by injection, preferably by systemic injection.

In one embodiment, the composition, pharmaceutical composition, nutraceutical composition or medicament according to the invention is administered by subcutaneous injection.

In one embodiment, the composition, pharmaceutical composition, nutraceutical composition or medicament according to the invention is administered by intraperitoneal injection.

Examples of formulation suitable for administration by injection include, but are not limited to, solutions, suspensions, solid forms for preparing a solution or suspensions for injection.

In one embodiment, the composition, pharmaceutical composition, nutraceutical composition or medicament according to the invention is administered at a dose adapted for each subject and determined by a qualified person.

It is thus specified that the daily dose of the composition, of the pharmaceutical composition, the nutraceutical composition or of the medicament according to the invention will be decided by the attending physician in the context of sound medical practice. This dose as defined for a particular subject may vary as a function of various factors including in particular: the disease and its severity; the composition used; the subject's age, weight, health, sex and diet; the time of administration; the route of administration; the duration of treatment; other drugs used in parallel or in combination with the composition, the pharmaceutical composition, the nutraceutical composition or the medicament according to the invention and every related factors known in the context of medical practice. For example, it is possible to start treatment at a dose lower than that required to achieve the desired therapeutic effect and then gradually increase the dosage until the desired therapeutic effect is obtained. Conversely, it may be advisable to start treatment with a bolus (or loading dose) so that the desired plasma concentration is quickly reached and then the elimination is compensated for by administration of maintenance doses.

In one embodiment, the composition, pharmaceutical composition, nutraceutical composition or medicament according to the invention is administered at least once a day, at least twice a day, at least three times a day.

In one embodiment, the composition, pharmaceutical composition, nutraceutical composition or medicament according to the invention is administered every two, three, four, five, six days.

In one embodiment, the composition, pharmaceutical composition, nutraceutical composition or medicament is administered twice a week, once a week, every two weeks, every three weeks, once a month.

In one embodiment, the composition, pharmaceutical composition, nutraceutical composition or medicament according to the invention is administered every month, every two months, every three months, every four months, every five months, every six months, once a year.

In one embodiment, the composition, pharmaceutical composition, nutraceutical composition or medicament according to the invention is administered over a period of about one day, two days, three days, four days, five days, six days, one week, two weeks, three weeks, one month, two months, three months, six months, one year, or during a longer period, for example for several years or during the whole of the remaining life of the subject.

In one embodiment, the composition, pharmaceutical composition, nutraceutical composition or medicament according to the invention is administered until treatment or improvement of symptoms associated with the cardiometabolic disease, preferably with the metabolic disease related to glucose intolerance and/or insulin resistance.

In one embodiment, the composition, pharmaceutical composition, nutraceutical composition or medicament according to the invention is administered in the frame of a chronic treatment. In one embodiment, the composition, the pharmaceutical composition, the nutraceutical composition or the medicament according to the invention is administered in the frame of an acute treatment.

In an alternative embodiment, the composition, pharmaceutical composition, nutraceutical composition or medicament according to the invention is administered pro re nata, i.e., as needed. The terms "administered as needed" and "pro re nata", as used herein, refer to those compositions, pharmaceutical compositions, nutraceutical compositions or medicament for which the dosage and frequency of administration are left to the discretion of the subject, as opposed to compositions which must be administered at a fixed regimen and frequency.

In one embodiment, the daily dose of *Moricandia* in the composition, pharmaceutical composition, nutraceutical composition or medicament according to the invention which can or should be administered to the subject ranges from about 10 mg/kg to about 500 mg/kg, about 50 mg/kg to about 450 mg/kg, about 100 mg/kg to about 400 mg/kg, about 150 mg/kg to about 350 mg/kg, about 175 mg/kg to about 325 mg/kg, about 200 mg/kg to about 300 mg/kg, about 225 mg/kg to about 275 mg/kg, from about 240 mg/kg to about 260 mg/kg. In one embodiment, the daily dose of the composition, pharmaceutical composition, nutraceutical composition or medicament according to the invention which can or should be administered to the subject is about 250 mg/kg.

In one embodiment, the daily human equivalent dose of *Moricandia* in the composition, pharmaceutical composition, nutraceutical composition or medicament of the invention which can or should be administered to the subject ranges from about 1 mg/kg to about 80 mg/kg, from about 7.5 mg/kg to about 72.5 mg/kg, from about 15 mg/kg to about 65 mg/kg, from about 22.5 mg/kg to about 57.5 mg/kg, about 27.5 mg/kg to about 52.5 mg/kg, about 32.5 mg/kg to about 47.5 mg/kg, about 37.5 mg/kg to about 42.5 mg/kg, from about 39 mg/kg to about 41 mg/kg. In one embodiment, the daily dose of the composition, pharmaceutical composition, nutraceutical composition or medicament according to the invention which can or should be administered to the subject is about 40 mg/kg.

In one embodiment, the daily dose of *Astragalus* in the composition, pharmaceutical composition, nutraceutical composition or medicament of the invention which can or should be administered to the subject ranges from about 10 mg/kg to about 500 mg/kg, about 50 mg/kg to about 450 mg/kg, about 100 mg/kg to about 400 mg/kg, about 150 mg/kg to about 350 mg/kg, about 175 mg/kg to about 325 mg/kg, about 200 mg/kg to about 300 mg/kg, about 225 mg/kg to about 275 mg/kg, from about 240 mg/kg to about 260 mg/kg. In one embodiment, the daily dose of the composition, pharmaceutical composition, nutraceutical composition or medicament according to the invention which can or should be administered to the subject is about 250 mg/kg.

In one embodiment, the daily human equivalent dose of *Astragalus* in the composition, pharmaceutical composition, nutraceutical composition or medicament of the invention which can or should be administered to the subject ranges from about 1 mg/kg to about 80 mg/kg, from about 7.5 mg/kg to about 72.5 mg/kg, from about 15 mg/kg to about 65 mg/kg, from about 22.5 mg/kg to about 57, 5 mg/kg, about 27.5 mg/kg to about 52.5 mg/kg, about 32.5 mg/kg to about 47.5 mg/kg, about 37.5 mg/kg to about 42.5 mg/kg, from about 39 mg/kg to about 41 mg/kg. In one embodiment, the daily dose of the composition, pharmaceutical composition, nutraceutical composition or medicament according to the invention which can or should be administered to the subject is about 40 mg/kg.

In one embodiment, the daily doses described above correspond to the doses of *Moricandia* and/or *Astragalus* plant material, preferably to the doses of *Moricandia* and/or *Astragalus* dry plant material.

In a preferred embodiment, the daily doses described above correspond to the doses of extract of *Moricandia* and/or *Astragalus* obtained after extraction as described above; preferably by dehydration, air drying, microwave drying, oven drying, lyophilization, filtration, grinding, maceration, percolation, infusion, decoction, Soxhlet extraction, hot continuous extraction, micro-assisted extraction, ultrasound-assisted extraction, accelerated solvent extraction, extraction by supercritical fluid, aqueous extraction, alcoholic extraction, steam distillation, enfleurage, enzymatic digestion or a combination of two or more of these techniques; more preferably, by decoction or maceration; even more preferably, by lyophilization after decoction or maceration.

In one embodiment, the subject is human.

In one embodiment, the subject has been diagnosed, or is at risk of being diagnosed, with a cardiometabolic disease, preferably with a metabolic disease related to glucose intolerance and/or insulin resistance.

In one embodiment, the subject is prediabetic. In one embodiment, the subject is diabetic.

By "prediabetic" is meant a condition characterized by a glycemia level higher than normal, but not enough to establish the diagnosis of diabetes. Typically, a subject is diagnosed as being "prediabetic" when their fasting glycemia level is between 6.1 and 6.9 mmol/L; or their blood glycated hemoglobin level is between 6.0 and 6.4%; and/or their glycemia level, measured two hours after ingestion of 75 g of glucose, is between 7.8 and 11.0 mmol/L.

In one embodiment, the subject is at high risk of developing type 2 diabetes. Examples of risk factors associated with type 2 diabetes include, but are not limited to, prediabetic condition, arterial hypertension, male gender, age over 40, large waist circumference, low physical activity, sugar-rich and/or fat-rich diet and predispositions related to heredity (genetic and environmental).

EXAMPLES

The present invention will be better understood in the light of the following examples which illustrate the invention in a non-limitative manner Example 1

Harvesting and Preparation of Extracts of *Moricandia arvensis* and *Astragalus armatus*

An extract of *Moricandia arvensis* was prepared by decoction, by immersing 100 g of dried and powdered leaves in 1 liter of boiling water for 15 to 20 minutes. After filtration of the decoction, the extract was lyophilized. The lyophilizate was then stored at 4° C.

An extract of *Astragalus armatus* was prepared by maceration, by immersing 100 g of dried and powdered roots in 1 liter of methanol for 15 days with stirring. After filtration of the macerate, methanol was evaporated under reduced pressure with a rotary evaporator at 40° C. until a dry extract (powder) was obtained. The dry extract was then stored at 4° C.

Example 2

Pharmacological Effects of Extracts of *Moricandia arvensis* and *Astragalus armatus* in a Development Model of Type 2 Diabetes Materials and Methods Animals and Study Protocol Wistar rats (Charles River laboratories, USA) were divided into 3 groups for a study protocol lasting 26 days:
- the rats of group 1 followed a standard diet (SAFE laboratories, France);
- the rats of group 2 were fed an HFHS diet ("High Fat High Sucrose"—reference H235, SAFE laboratories, France) which leads to symptoms of type 2 diabetes;
- the rats of group 3 were fed an HFHS diet and were treated every morning by gavage with 250 mg/kg with an extract of *Moricandia arvensis* (HFHS-MA) or of *Astragalus armatus* (HFHS-AA) prepared as described in Example 1 above.

Glycemia was measured at the start of the protocol (day 0), at the end of week 1 (day 7), at the end of week 2 (day 14) and at the end of week 3 (day 21). Several tests were then carried out in a period of 5 days at the end of the protocol (days 22 to 26—2-day rest interval between each of the tests). Basal insulinemia was measured. An oral glucose tolerance test, OGTT (oral hyperglycemia −2 g/kg) was performed. Glycemia and insulinemia were measured during this test. An insulin sensitivity test (intraperitoneally) (1 U/kg) was also performed. The body composition was analyzed by magnetic resonance imaging (EchoMRI) for groups 1 and 2, and for animals of group 3 treated with an extract of *Moricandia arvensis* on day 26 of the study protocol, after the end of the tests. The rats were weighed on days 0, 5, 9, 15, 18, 23, 25 and 26 of the study protocol.

Statistical Analysis

The values of the means±standard error of the mean (SEM), during and/or at the end of the treatment, are presented. The size is n=8 rats/group, except for the measurement of basal glycemia and insulinemia for which n=9 to 11. Statistical calculations to assess the differences between the groups (significance level: p<0.05) were performed by a 2-way ANOVA analysis of variance (time/treatment effect). Statistical analyzes were performed using Prism software. Significant differences are shown in the figures.

Results

Treatment with an extract of *Moricandia arvensis* or an extract of *Astragaius armatus* prevents hyperglycemia observed in untreated animals fed the HFHS diet (FIG. 1 and Table 1).

TABLE 1

Glycemia at the end of week 3 (day 21) for the different groups.

| Group | Glycemia (mM ± SEM) | Glycemia (g/L ± SEM) |
|---|---|---|
| STD | 6.17 ± 0.17 | 1.10 ± 0.03 |
| HFHS | 7.98 ± 0.25 | 1.43 ± 0.04 |
| HFHS-MA | 6.52 ± 0.16 | 1.17 ± 0.03 |
| HFHS-AA | 6.16 ± 0.15 | 1.10 ± 0.03 |

Figure 2:
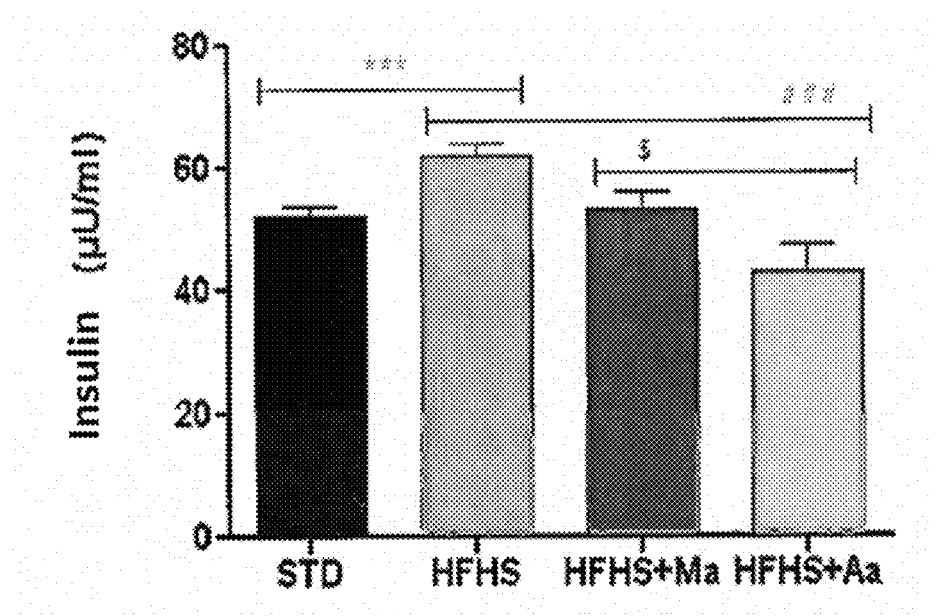
FIG. 2 is a histogram showing the basal insulinemia after 3 weeks of the study protocol in the different groups of rats as defined in the legend of FIG. 1.
***$p<0.001$
$p<0.001$
$ $p<0.05$
2-way ANOVA test.
Figure 3A:
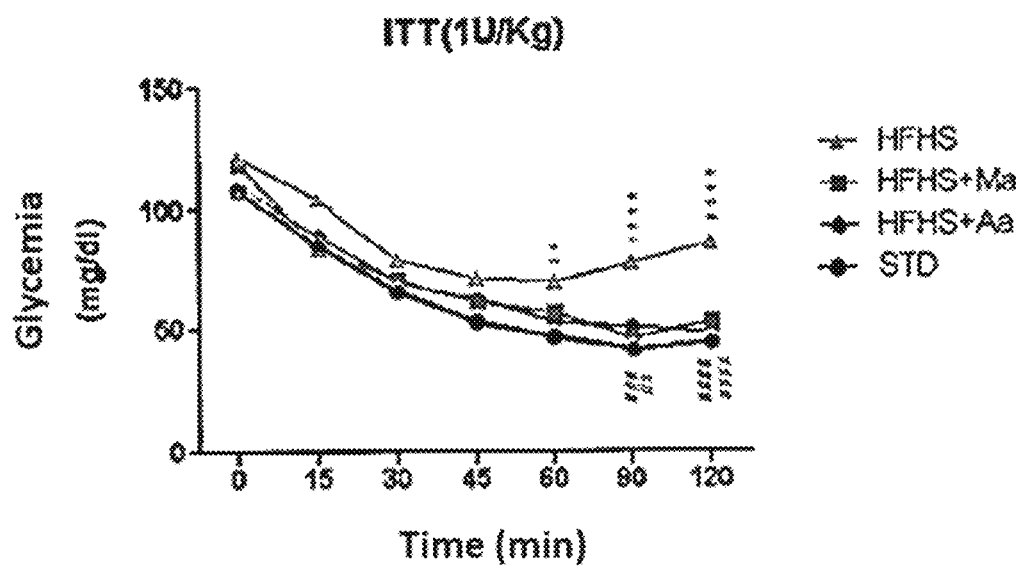
FIGS. 3A and 3B shows the results of the insulin sensitivity test carried out at the end of the 3 weeks of the study protocol in the different groups of rats as defined in the legend of FIG. 1.
Figure 3B:
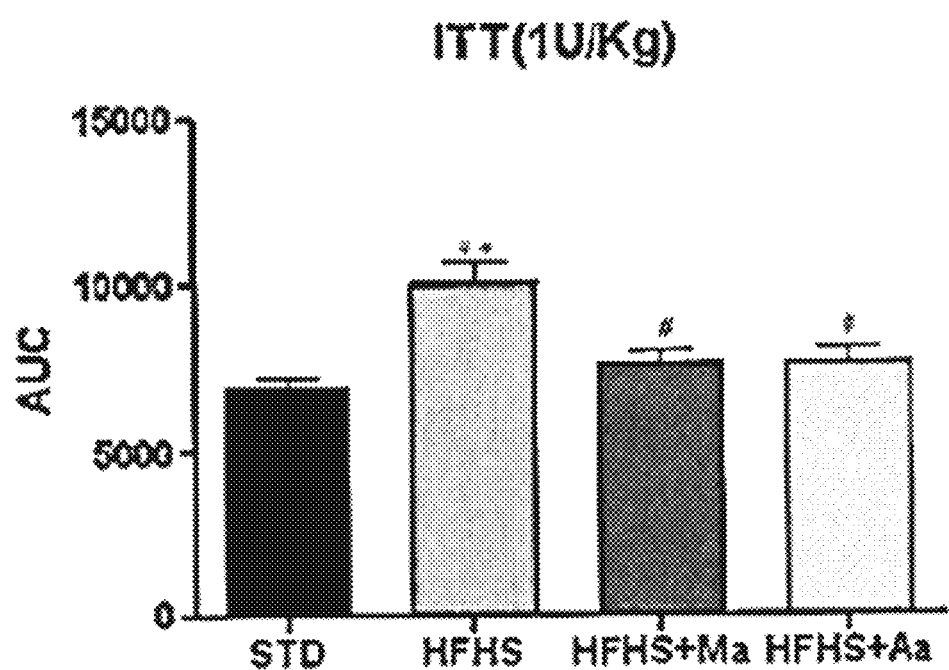

The measurement of basal insulinemia at the end of the protocol (FIG. 2 and Table 2) and the results of the insulin sensitivity test (FIGS. 3A and 3B; Tables 3 and 4) show that the treatment with an extract of *Moricandia arvensis* or an extract of *Astragalus armatus* prevents the development of insulin resistance, seen in untreated animals fed the HFHS diet.

TABLE 2

Basal insulinemia at the end of the protocol for the different groups.

| Group | Insulin levels (μU/mL ± SEM) |
|---|---|
| STD | 52.0 ± 0.16 |
| HFHS | 62.2 ± 2.00 |
| HFHS-MA | 53.4 ± 2.6 |
| HFHS-AA | 42.7 ± 4.4 |

TABLE 3

Glycemia at 120 minutes after the insulin injection during the insulin sensitivity test for the different groups.

| Group | Glycemia (μU/mL ± SEM) |
|---|---|
| STD | 52.0 ± 0.16 |
| HFHS | 62.2 ± 2.00 |
| HFHS-MA | 53.4 ± 2.6 |
| HFHS-AA | 42.7 ± 4.4 |

TABLE 4

Area under the glycemia trend curves during the insulin sensitivity test.

| Group | Area Under Curve (arbitrary surface unit ± SEM) |
|---|---|
| STD | 6951 ± 351 |
| HFHS | 9965 ± 654 |
| HFHS-MA | 7634 ± 375 |
| HFHS-AA | 7479 ± 493 |

The glucose tolerance test shows that treatment with an extract of *Moricandia arvensis* or an extract of *Astragalus armatus* prevents the development of glucose intolerance, observed in untreated animals fed with the HFHS diet (FIGS. 4A and 4B; Tables 5 and 6). Measurement of insulinemia during the glucose tolerance test shows that the insulin level does not change in animals of group 3 treated with an extract of *Moricandia arvensis* (FIG. 4C; Table 7). This observation suggests that the effect of *Moricandia arvensis* extract on glycemia is mediated by the preservation of insulin sensitivity. In animals treated with an extract of *Astragalus armatus*, insulinemia is equivalent to that measured in the control group, fed a standard diet (FIG. 4C). This finding indicates that treatment with an extract of *Astragalus armatus*, in addition to its effect on insulin sensitivity, also prevents the decrease in insulin secretion capacity observed in untreated animals fed the HFHS diet.

TABLE 5

Glycemia during the glucose tolerance test.

| | Glycemia (mg/dl. ± SEM) Time | | | | |
|---|---|---|---|---|---|
| Group | 15 minutes | 45 minutes | 60 minutes | 90 minutes | 120 minutes |
| STD | — | 144.4 ± 5.5 | 141.8 ± 3.9 | 135.2 ± 1.8 | — |
| HFHS | 180.3 ± 5.9 | 173.9 ± 3.5 | 175.9 ± 5.1 | 160.0 ± 3.1 | 143.5 ± 4.9 |
| HFHS-MA | 154.4 ± 5.5 | 150.3 ± 6.0 | 146.0 ± 4.7 | 129.3 ± 4.9 | 118.0 ± 3.1 |
| HFHS-AA | — | 150.6 ± 4.5 | 138.3 ± 3.9 | 128.1 ± 3.8 | 116.5 ± 1.6 |

TABLE 6

Area under the glycemia trend curves during the glucose tolerance test in the 0-60-minute time interval.

| Group | Area under the curve (arbitrary surface unit ± SEM) |
|---|---|
| STD | 8882 ± 273 |
| HFHS | 10100 ± 92 |
| HFHS-MA | 8686 ± 284 |
| HFHS-AA | 8899 ± 230 |

TABLE 7

Insulinemia during the glucose tolerance test at time +15 minutes.

| Group | Insulin levels (μU/mL ± SEM) |
|---|---|
| STD | 67.2 ± 5.1 |
| HFHS | 46.3 ± 5.1 |
| HFHS-MA | 45.1 ± 5.1 |
| HFHS-AA | 74.4 ± 4.5 |

Analysis of body composition shows that treatment with an extract of *Moricandia arvensis* prevents the increase in the proportion of body fat mass (and the decrease in the proportion of associated lean body mass) observed in untreated animals fed the HFHS diet (FIGS. 5A and 5B; Table 8). This finding indicates a potential mechanism related to the development of body fat mass underlying the preservation of insulin sensitivity in animals treated with an extract of *Moricandia arvensis*.

TABLE 8

Analysis of body composition.

| Group | Fat mass (% of total weight without water ± SEM) | Lean body mass (% of total weight without water ± SEM) |
|---|---|---|
| STD | 13.7 ± 0.7 | 72.5 ± 0.7 |
| HFHS | 20.0 ± 1.1 | 66.9 ± 1.0 |
| HFHS-MA | 16.3 ± 0.9 | 71.7 ± 1.9 |

The weighing of the animals in the 3 groups during the study protocol shows that the treatment with an extract of *Moricandia arvensis* or an extract of *Astragalus armatus* prevents weight gain observed in untreated animals fed with the HFHS diet (FIG. 6 and Table 9).

TABLE 9

Evolution of the difference in weight on days 9, 18, 23 and 26.

| | Weight delta (g ± SEM) Day | | |
|---|---|---|---|
| Group | 9 | 18 | 23 |
| STD | 26.8 ± 1.7 | 40.4 ± 2.2 | 65.1 ± 3.0 |
| HFHS | 45.5 ± 5.0 | 81.0 ± 5.7 | 101.6 ± 7.8 |
| HFHS-MA | 29.6 ± 3.3 | 52.1 ± 4.4 | 68.4 ± 7.0 |
| HFHS-AA | 28.4 ± 1.8 | 52.9 ± 2.7 | 79.0 ± 2.9 |

Conclusion

These results, taken as a whole, show that treatment with an extract of *Moricandia arvensis* or an extract of *Astragalus armatus* prevents hyperglycemia, insulin resistance, glucose intolerance and the weight gain observed in a model developing symptoms of type 2 diabetes.

In the case of treatment with an extract of *Astragalus armatus*, it appears that this also preserves the insulin secretion capacity, which is reduced when the animals are fed the HFHS diet.

Example 3

Influence of Extracts of *Moricandia arvensis* and *Astragalus armatus* on the Capacity for Insulin Secretion by Pancreatic Islets of Rats in Primary Culture Materials and Methods Pancreatic islets from C57Bl6 mice were isolated by size, distributed into culture wells (taking care to respect an equivalent distribution in each well in terms of size) and cultured under normal condition (control) or under lipotoxic condition in the presence of palmitate:
[Control]: culture medium alone;
[Palmitate]: culture medium+0.5 mM palmitate (saturated fatty acid mimicking diabetic conditions—DT2);
[Palmitate+FM50]: culture medium+0.5 mM palmitate+ 50 μg/mL of extract of *Moricandia arvensis;*
[Palmitate+FM100]: culture medium+0.5 mM palmitate+ 100 μg/mL of extract of *Moricandia arvensis;*
[Palmitate+RA50]: culture medium+0.5 mM palmitate+ 50 μg/mL of extract of *Astragalus armatus;*
[Palmitate+RA100]: culture medium+0.5 mM palmitate+ 100 μg/mL of extract of *Astragalus armatus;*

Extracts of *Moricandia arvensis* and *Astragalus armatus* were prepared as described in Example 1 above.

After 72 hours of culture, the insulin secretion capacity of the pancreatic islets was tested by measuring the concentration of insulin before and after stimulation by an increase in glucose concentration in the medium from 2.8 mM (basal condition) to 16.7 mM (stimulated condition).

Results

The basal secretion capacity and after stimulation of the pancreatic islets, reduced in the presence of palmitate, is largely preserved by the presence of an extract of *Moricandia arvensis* or *Astragalus armatus* in the medium (FIG. 7 and Table 10).

TABLE 10

Insulin secretion by the pancreatic islets.

| | Insulin secretion (ng/islet/h ± SEM) Simulation | |
|---|---|---|
| Culture condition | No | Yes |
| Control | 0.126 ± 0.010 | 2.869 ± 0.066 |
| Palmitate | 0.084 ± 0.016 | 1.845 ± 0.0183 |
| Palmitate + FM50 | 0.118 ± 0.014 | 2.525 ± 0.280 |
| Palmitate + FM100 | 0.141 ± 0.002 | 2.430 ± 0.255 |
| Palmitate + RA50 | 0.117 ± 0.016 | 2.279 ± 0.163 |
| Palmitate + RA100 | 0.126 ± 0.011 | 2.349 ± 0.324 |

Conclusion

These results indicate a protective effect of extracts of *Moricandia arvensis* and *Astragalus armatus* on the capacity of insulin secretion by pancreatic cells, and thus the onset of type 2 diabetes in the event of a sugar-rich and fat-rich diet.

Example 4

Curative Effects of MA in a Genetic Model of Type 2 Diabetes (Zücker ZDF Rat)

Materials and Methods

Animals and Study Protocol

The anti-diabetic effects of MA extracts were tested in a severe T2D model: the ZDF rat (Zücker diabetic fatty rat), a genetic model which exhibits a recessive mutation of the leptin receptor (only animals carrying the mutation on both alleles develop obesity and T2D). This total resistance to leptin leads to overeating, massive obesity and insulin resistance which are irreversible: diabetes sets in and continues to increase with age. First, hyperinsulinemia develops at weaning (at 3 weeks of age) to compensate for tissue resistance, but the endocrine pancreas becomes depleted and the animals quickly become diabetic, as their insulin secretion declines and eventually breaks down.

It is in this model that the extracts of MA were tested, under the same conditions as for the preventive effects of the preceding Examples (250 mg/kg, by daily gavage, for 8 to 13 weeks).

The 6-week-old animals were divided into 3 groups for a 13-week study protocol:

ZDF Lean (fa/+): control, heterozygous for the recessive mutation or homozygous for the wild-type leptin receptor allele. This is the normal reference group.

ZDF DB (fa/fa): homozygous for the leptin receptor mutation. The animals are obese, insulin resistant and then irreversibly diabetic.

ZDF DB (fa/fa)+MA: homozygous for the leptin receptor mutation, treated by gavage with 250 mg/kg of an extract of *Moricandia arvensis* prepared as described in Example 1 above.

The animals are on a normal diet (SAFE). The various measurements and tests were carried out during the 8 to 13 weeks.

Statistical Analysis

The size per group is n=6. Results are presented as the mean±standard error of the mean (SEM). Statistical analyzes are analyzes of variance (ANOVA), with a significance level at $p<0.05$. Significant differences are shown in the figures.

Results

Treatment with an extract of *Moricandia arvensis* decreases hyperglycemia observed from week 3 in untreated leptin receptor mutation homozygotes (FIG. 8 and Table 11).

TABLE 11

Glycemia at week 11 of the study protocol.

| Group | Glycemia (mg/dL ± SEM) |
|---|---|
| ZDF lean | 116.5 ± 3.6 |
| ZDF DB | 525.8 ± 20.2 |
| ZDF DB + MA | 454.1 ± 30.3 |

Figure 10A:
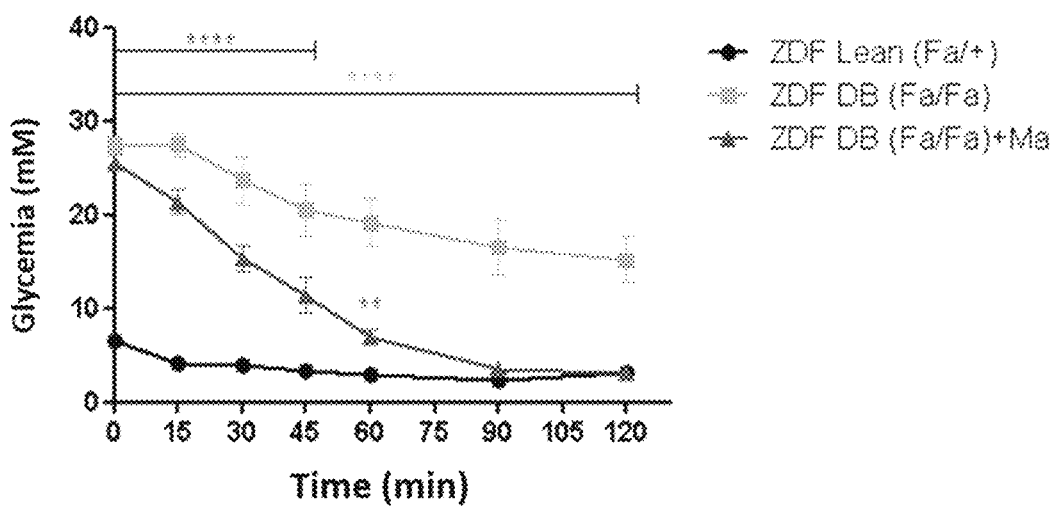
Figure 10B:
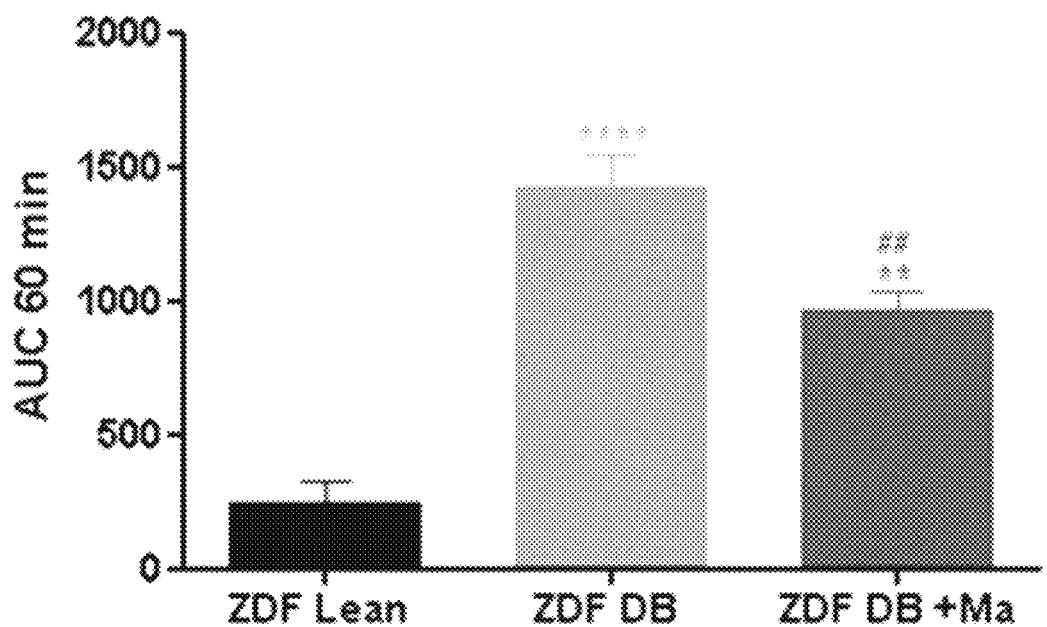

The measurement of basal insulinemia during the first 8 weeks of the protocol (FIG. 9 and Table 12) and the results of the insulin sensitivity test (FIGS. 10A and 10B; Table 13) show that treatment with an extract of *Moricandia arvensis* treats the insulin resistance observed in untreated leptin receptor mutant homozygotes.

TABLE 12

Area under the basal insulinemia trend curves during the first 8 weeks of the protocol.

| Group | Area under the curve (arbitrary surface unit ± SEM) |
|---|---|
| ZDF lean | 8.11 ± 0.17 |
| ZDF DB | 13.76 ± 0.76 |
| ZDF DB + MA | 12.03 ± 0.92 |

TABLE 13

Area under the glycemia trend curves during the first 60 minutes of the insulin sensitivity test.

| Group | Area under the curve (arbitrary surface unit ± SEM) |
|---|---|
| ZDF lean | 243.5 ± 33.9 |
| ZDF DB | 1424.0 ± 119.9 |
| ZDF DB + MA | 964.9 ± 71.4 |

The glucose tolerance test shows that treatment with an extract of *Moricandia arvensis* makes it possible to reduce the glucose intolerance observed in untreated leptin receptor mutant homozygotes (FIGS. 11A and 11B; Table 14).

TABLE 14

Area under the glycemia trend curves in the first 60 minutes of the glucose tolerance test.

| Group | Area under the curve (arbitrary surface unit ± SEM) |
|---|---|
| ZDF lean | 1183.8 ± 8.5 |
| ZDF DB | 4371.0 ± 93.2 |
| ZDF DB + MA | 3472.8 ± 67.6 |

The lipid balance shows that the treatment with an extract of *Moricandia arvensis* makes it possible to reduce the level of cholesterol, triglycerides and high-density lipoprotein cholesterol (HDLC) abnormally high in untreated leptin receptor mutant homozygotes (FIG. 12 and Table 15). Given the inflammatory role of lipids and the role of inflammation in the development of insulin resistance, one of the potential effects of *Moricandia arvensis* could be to improve the lipid balance.

TABLE 15

Lipid balance.

| Group | Total cholesterol (mmol/L ± SEM) | Triglycerides (mmol/L ± SEM) |
|---|---|---|
| ZDF lean | 2.0 ± 0.1 | 1.4 ± 0.1 |
| ZDF DB | 4.4 ± 0.1 | 5.1 ± 0.4 |
| ZDF DB + MA | 3.9 ± 0.1 | 4.0 ± 0.3 |

Conclusions

These results, taken as a whole, show that the administration of an extract of *Moricandia arvensis* can curatively treat type 2 diabetes in this preclinical model.

Example 5

**Pharmacological Effects of a Combination of Extracts of *Moricandia arvensis* and *Astragalus armatus* in a Developmental Model of Type 2 Diabetes**

Materials and Methods

Animals and Study Protocol

Wistar rats (Charles River laboratories, USA) are divided into 3 groups for a study protocol lasting 26 days:
- the rats of group 1 follow a standard diet (SAFE laboratories, France);
- the rats of group 2 are fed an HFHS diet ("High Fat High Sucrose"—reference H235, SAFE laboratories, France) which leads to the symptoms of type 2 diabetes;
- the rats of group 3 were fed an HFHS diet, and were treated every morning by gavage with 250 mg/kg of a combination of extracts of *Moricandia arvensis* and *Astragalus armatus* (HFHS-MA+AA).

The glycemia is measured at the start of the protocol (day 0), at the end of week 1 (day 7), at the end of week 2 (day 14) and at the end of week 3 (day 21). Several tests are then carried out in a period of 5 days at the end of the protocol (days 22 to 26 -2-day rest interval between each of the tests). Basal insulinemia is measured. An oral glucose tolerance test, OGTT (oral hyperglycemia -2 g/kg) is performed. Glycemia and insulinemia are measured during this test. An insulin sensitivity test (intraperitoneally) (1 U/kg) is also performed. Body composition is analyzed by magnetic resonance imaging (EchoMRI) for groups 1 and 2, and for group 3 animals treated with a combination of extracts of *Moricandia arvensis* and *Astragalus armatus* on day 26 of the study protocol, after the end of the tests. Rats are weighed on days 0, 5, 9, 15, 18, 23, 25 and 26 of the study protocol.

Example 6

**Influence of a Combination of Extracts of *Moricandia arvensis* and *Astragalus armatus* on the Capacity for Insulin Secretion by Pancreatic Islets of Rats in Primary Culture**

Materials and Methods

Pancreatic islets from C57Bl6 mice were isolated by size, distributed into culture wells (taking care to respect an equivalent distribution in each well in terms of size) and cultured under normal condition (control) or under lipotoxic condition in the presence of palmitate:
- [Control]: culture medium alone;
- [Palmitate]: culture medium+0.5 mM palmitate (saturated fatty acid mimicking diabetic conditions—DT2);
- [Palmitate+FM50]: culture medium+0.5 mM palmitate+ 50 µg/mL of extract of *Moricandia arvensis;*
- [Palmitate+FM100]: culture medium+0.5 mM palmitate+ 100 µg/mL of extract of *Moricandia arvensis;*
- [Palmitate+RA50]: culture medium+0.5 mM palmitate+ 50 µg/mL of extract of *Astragalus armatus;*
- [Palmitate+RA100]: culture medium+0.5 mM palmitate+ 100 µg/mL of extract of *Astragalus armatus;*

Extracts of *Moricandia arvensis* and *Astragalus armatus* are prepared as described in Example 1 above.

After 72 hours of culture, the insulin secretion capacity of the pancreatic islets is tested by measuring the concentration of insulin before and after stimulation by an increase in the concentration of glucose in the medium from 2.8 mM (basal condition) to 16.7 mM (stimulated condition).

Example 7

**Curative Effects of a Combination of Extracts of *Moricandia arvensis* and *Astragalus armatus* in a Genetic Model of Type 2 Diabetes (Zücker ZDF Rat)**

Materials and Methods

Animals and Study Protocol

The anti-diabetic effects of MA extracts are tested in a severe T2D model: the ZDF rat (Zücker diabetic fatty rat), a genetic model which exhibits a recessive mutation of the leptin receptor (only animals carrying the mutation on both alleles develop obesity and T2D). This total resistance to leptin leads to overeating, massive obesity and insulin resistance which are irreversible: diabetes sets in and continues to increase with age. First, hyperinsulinemia develops at weaning (at 3 weeks of age) to compensate for tissue resistance, but the endocrine pancreas becomes depleted and the animals quickly become diabetic, as their insulin secretion declines and eventually breaks down.

It is in this model that the extracts of *Moricandia arvensis* and *Astragalus armatus* are tested, under the same conditions as for the preventive effects of the preceding Examples (250 mg/kg, by daily gavage, for 8 to 13 weeks).

The 6-week-old animals are divided into 3 groups for a 13-week study protocol:
- ZDF Lean (fa/+): control, heterozygous for the recessive mutation or homozygous for the wild-type leptin receptor allele. This is the normal reference group.
- ZDF DB (fa/fa): homozygous for the leptin receptor mutation. The animals are obese, insulin resistant and then irreversibly diabetic.
- ZDF DB (fa/fa)+MA: homozygous for the leptin receptor mutation, treated by gavage with 250 mg/kg of an extract of *Moricandia arvensis* prepared as described in Example 1 above.

The animals are on a normal diet (SAFE). The various measurements and tests are carried out during the 8 to 13 weeks.

The invention claimed is:

1. A method of treating a metabolic disease selected from the group consisting of insulin resistance or deficiency, glucose intolerance, hyperglycemia, and obesity, in a subject having type 2 diabetes, comprising administering to said subject a composition comprising an effective amount of an extract of *Moricandia arvensis*.

2. The method according to claim 1, wherein the extract of *Moricandia arvensis* is a decoction and/or a maceration of *Moricandia arvensis*.

3. The method according to claim 1, wherein the extract of *Moricandia arvensis* is a decoction of leaves of *Moricandia arvensis*.

4. The method according to claim 1, further comprising an extract of *Astragalus*.

5. The method according to claim 4, wherein *Astragalus* is *Astragalus armatus*.

6. The method according to claim 4, wherein the extract of *Astragalus* is a decoction and/or a maceration of *Astragalus*.

7. The method according to claim 4, wherein the extract of *Astragalus* is a maceration of *Astragalus* roots.

8. The method according to claim 4, wherein the extract of *Astragalus* is a maceration of *Astragalus armatus* roots.

9. The method according to claim 4, wherein the extract of *Astragalus* is a methanolic maceration of *Astragalus armatus* roots.

10. A method of:
controlling weight gain in a subject;
controlling fat mass gain in a subject;
stimulating weight loss in a subject; or
stimulating fat mass loss in a subject;
comprising administering to said subject a composition comprising an effective amount of an extract of *Moricandia arvensis*, wherein the subject has type 2 diabetes.

11. The method according to claim 10, wherein the extract of *Moricandia arvensis* is a decoction and/or a maceration of *Moricandia arvensis*.

12. The method according to claim 10, wherein the extract of *Moricandia arvensis* is a decoction of *Moricandia arvensis* leaves.

13. The method according to claim 10, further comprising an extract of *Astragalus*.

14. The method according to claim 1, wherein the extract of *Moricandia arvensis* is a lyophilized decoction of leaves of *Moricandia arvensis*.

15. The method according to claim 10, wherein the extract of *Moricandia arvensis* is a lyophilized decoction of *Moricandia arvensis* leaves.

* * * * *